United States Patent
Mueller et al.

(10) Patent No.: US 10,913,760 B2
(45) Date of Patent: Feb. 9, 2021

(54) CARBOHYDRATE BINDERS AND MATERIALS MADE THEREWITH

(71) Applicants: KNAUF INSULATION SPRL, Vise (BE); KNAUF INSULATION, INC., Shelbyville, IN (US)

(72) Inventors: Gert R. Mueller, New Albany, OH (US); Charles Fitch Appley, Cumberland, IN (US); Benedicte Pacorel, Auckland (NZ); Carl Hampson, St. Helens (GB)

(73) Assignees: Knauf Insulation, Inc., Shelbyville, IN (US); Knauf Insulation SPRL, Vise (BE)

( * ) Notice: Subject to any disclaimer, the term of this patent is extended or adjusted under 35 U.S.C. 154(b) by 0 days.

(21) Appl. No.: 16/425,301

(22) Filed: May 29, 2019

(65) Prior Publication Data
US 2019/0352323 A1  Nov. 21, 2019

Related U.S. Application Data

(63) Continuation of application No. 16/241,049, filed on Jan. 7, 2019, which is a continuation of application
(Continued)

(51) Int. Cl.
*C08G 12/00* (2006.01)
*C08G 14/00* (2006.01)
(Continued)

(52) U.S. Cl.
CPC .............. *C07H 5/06* (2013.01); *C03C 25/25* (2018.01); *C08G 12/00* (2013.01); *C08G 14/00* (2013.01); *C08G 16/00* (2013.01); *D21H 19/12* (2013.01)

(58) Field of Classification Search
None
See application file for complete search history.

(56) References Cited

U.S. PATENT DOCUMENTS

| 1,801,052 A | 4/1931 | Meigs |
| 1,801,053 A | 4/1931 | Meigs |

(Continued)

FOREIGN PATENT DOCUMENTS

| AU | 8538765 | 8/1985 |
| AU | 9640921 | 7/1997 |

(Continued)

OTHER PUBLICATIONS

MSDS for Hexamethylenediamine, Sigma-Aldrich, Jul. 27, 2015 (Year: 7271).*

(Continued)

*Primary Examiner* — Peter A Salamon
(74) *Attorney, Agent, or Firm* — Knauf Insulation, Inc.; James K. Blodgett

(57) ABSTRACT

A binder comprising a polymeric binder comprising the products of a carbohydrate reactant and nucleophile is disclosed. The binder is useful for consolidating loosely assembled matter, such as fibers. Fibrous products comprising fibers in contact with a carbohydrate reactant and a nucleophile are also disclosed. The binder composition may be cured to yield a fibrous product comprising fibers bound by a cross-linked polymer. Further disclosed are methods for binding fibers with the carbohydrate reactant and polyamine based binder.

19 Claims, 3 Drawing Sheets

Related U.S. Application Data

No. 15/276,283, filed on Sep. 26, 2016, now abandoned, which is a continuation of application No. 13/696,452, filed as application No. PCT/EP2011/057364 on May 7, 2011, now Pat. No. 9,493,603.

(60) Provisional application No. 61/332,452, filed on May 7, 2010.

(51) Int. Cl.
| | | |
|---|---|---|
| *C08G 16/00* | (2006.01) | |
| *C08L 5/00* | (2006.01) | |
| *C07H 5/06* | (2006.01) | |
| *C03C 25/25* | (2018.01) | |
| *D21H 19/12* | (2006.01) | |

(56) References Cited

U.S. PATENT DOCUMENTS

| | | |
|---|---|---|
| 1,886,353 A | 11/1932 | Novotny |
| 1,902,948 A | 3/1933 | Castle |
| 1,964,263 A | 6/1934 | Krenke |
| 2,198,874 A | 4/1940 | Leighton |
| 2,215,825 A | 9/1940 | Wallace |
| 2,261,295 A | 11/1941 | Schlack |
| 2,362,086 A | 11/1944 | Eastes |
| 2,371,990 A | 3/1945 | Hanford |
| 2,392,105 A | 1/1946 | Sussman |
| 2,442,989 A | 6/1948 | Sussman |
| 2,500,665 A | 3/1950 | Courtright |
| 2,518,956 A | 8/1950 | Sussman |
| 2,875,073 A | 2/1959 | Gogek |
| 2,894,920 A * | 7/1959 | Ramos ............... 523/447 |
| 2,965,504 A | 12/1960 | Gogek |
| 3,038,462 A | 6/1962 | Bohdan |
| 3,138,473 A * | 6/1964 | Ess ............... D21H 17/07 106/162.5 |
| 3,222,243 A | 12/1965 | Gaston |
| 3,231,349 A | 1/1966 | Stalego |
| 3,232,821 A | 2/1966 | Banks |
| 3,297,419 A | 1/1967 | Eyre, Jr. |
| 3,513,001 A | 5/1970 | Woodhead |
| 3,551,365 A | 12/1970 | Matalon |
| 3,733,405 A * | 5/1973 | Derrig ............... A23K 20/105 426/335 |
| 3,784,408 A | 1/1974 | Jaffe |
| 3,791,807 A | 2/1974 | Etzel |
| 3,802,897 A | 4/1974 | Bovier |
| 3,809,664 A | 5/1974 | Burr |
| 3,826,767 A | 7/1974 | Hoover |
| 3,856,606 A | 12/1974 | Fan |
| 3,867,119 A | 2/1975 | Takeo |
| 3,907,724 A | 9/1975 | Higginbottom |
| 3,911,048 A | 10/1975 | Nistri |
| 3,919,134 A | 11/1975 | Higginbottom |
| 3,922,466 A | 11/1975 | Bell |
| 3,955,031 A * | 5/1976 | Jones ............... E04B 1/74 442/412 |
| 3,956,204 A | 5/1976 | Higginbottom |
| 3,961,081 A | 6/1976 | McKenzie |
| 3,971,807 A | 7/1976 | Brack |
| 4,014,726 A | 3/1977 | Fargo |
| 4,028,290 A | 6/1977 | Reid |
| 4,048,127 A | 9/1977 | Gibbons |
| 4,054,713 A | 10/1977 | Sakaguchi |
| 4,085,076 A | 4/1978 | Gibbons |
| 4,090,919 A * | 5/1978 | Chibata ............... C07H 13/12 210/679 |
| 4,097,427 A | 6/1978 | Aitken |
| 4,107,379 A | 8/1978 | Stofko |
| 4,109,057 A | 8/1978 | Nakamura |
| 4,144,027 A * | 3/1979 | Habib ............... 8/127.6 |
| 4,148,765 A | 4/1979 | Nelson |
| 4,183,997 A | 1/1980 | Stofko |
| 4,184,986 A | 1/1980 | Krasnobajew |
| 4,186,053 A | 1/1980 | Krasnobajew |
| 4,201,247 A | 5/1980 | Shannon |
| 4,201,857 A | 5/1980 | Krasnobajew |
| 4,217,414 A | 8/1980 | Walon |
| 4,233,432 A | 11/1980 | Curtis, Jr. |
| 4,246,367 A | 1/1981 | Curtis, Jr. |
| 4,259,190 A | 3/1981 | Fahey |
| 4,265,963 A | 5/1981 | Matalon |
| 4,278,573 A | 7/1981 | Tessler |
| 4,296,173 A | 10/1981 | Fahey |
| 4,301,310 A | 11/1981 | Wagner |
| 4,310,585 A | 1/1982 | Shannon |
| 4,322,523 A | 3/1982 | Wagner |
| 4,330,443 A | 5/1982 | Rankin |
| 4,333,484 A | 6/1982 | Keritsis |
| 4,357,194 A | 11/1982 | Stofko |
| 4,361,588 A | 11/1982 | Herz |
| 4,379,101 A | 4/1983 | Smith |
| 4,393,019 A | 7/1983 | Geimer |
| 4,396,430 A | 8/1983 | Matalon |
| 4,400,496 A | 8/1983 | Butler |
| 4,464,523 A | 8/1984 | Neigel |
| 4,485,020 A * | 11/1984 | Shay ............... C08B 37/0033 166/246 |
| 4,506,684 A | 3/1985 | Keritsis |
| 4,520,143 A * | 5/1985 | Jellinek ............... 523/410 |
| 4,524,164 A | 6/1985 | Viswanathan |
| 4,631,226 A * | 12/1986 | Jellinek ............... 442/106 |
| 4,654,259 A | 3/1987 | Stofko |
| 4,668,716 A | 5/1987 | Pepe |
| 4,692,478 A | 9/1987 | Viswanathan |
| 4,714,727 A | 12/1987 | Hume, III |
| 4,720,295 A | 1/1988 | Bronshtein |
| 4,734,996 A | 4/1988 | Kim |
| 4,754,056 A | 6/1988 | Ansel |
| 4,761,184 A | 8/1988 | Markessini |
| 4,780,339 A | 10/1988 | Lacourse |
| 4,828,643 A | 5/1989 | Newman |
| 4,845,162 A | 7/1989 | Schmitt |
| 4,906,237 A | 3/1990 | Johansson |
| 4,912,147 A | 3/1990 | Pfoehler |
| 4,918,861 A | 4/1990 | Carpenter |
| 4,923,980 A | 5/1990 | Blomberg |
| 4,929,722 A * | 5/1990 | Partain, III ............... A61K 8/736 210/500.27 |
| 4,950,444 A | 8/1990 | Deboufie |
| 4,988,780 A | 1/1991 | Das |
| 4,992,519 A | 2/1991 | Mukherjee |
| 5,001,202 A | 3/1991 | Denis |
| 5,013,405 A | 5/1991 | Izard |
| 5,032,431 A | 7/1991 | Conner |
| 5,037,930 A | 8/1991 | Shih |
| 5,041,595 A | 8/1991 | Yang |
| 5,089,342 A | 2/1992 | Dhein |
| 5,095,054 A | 3/1992 | Lay |
| 5,106,615 A | 4/1992 | Dikstein |
| 5,114,004 A | 5/1992 | Isono |
| 5,123,949 A | 6/1992 | Thiessen |
| 5,124,369 A | 6/1992 | Vandichel |
| 5,128,407 A | 7/1992 | Layton |
| 5,143,582 A | 9/1992 | Arkens |
| 5,151,465 A | 9/1992 | Le-Khac |
| 5,167,738 A | 12/1992 | Bichot |
| 5,198,492 A | 3/1993 | Stack |
| 5,217,741 A | 6/1993 | Kawachi |
| 5,218,048 A | 6/1993 | Abe |
| 5,240,498 A | 8/1993 | Matalon |
| 5,278,222 A | 1/1994 | Stack |
| 5,300,144 A | 4/1994 | Adams |
| 5,300,192 A | 4/1994 | Hansen |
| 5,308,896 A | 5/1994 | Hansen |
| 5,318,990 A | 6/1994 | Strauss |
| 5,336,753 A | 8/1994 | Jung |
| 5,336,755 A | 8/1994 | Pape |
| 5,336,766 A | 8/1994 | Koga |
| 5,340,868 A | 8/1994 | Strauss |
| 5,352,480 A | 10/1994 | Hansen |
| 5,367,849 A | 11/1994 | Bullock |

(56) References Cited

U.S. PATENT DOCUMENTS

| | | |
|---|---|---|
| 5,371,194 A | 12/1994 | Ferretti |
| 5,387,665 A | 2/1995 | Misawa |
| 5,389,716 A | 2/1995 | Graves |
| 5,393,849 A | 2/1995 | Srinivasan |
| 5,416,139 A | 5/1995 | Zeiszler |
| 5,421,838 A | 6/1995 | Gosset |
| 5,424,418 A | 6/1995 | Duflot |
| 5,434,233 A | 7/1995 | Kiely |
| 5,447,977 A | 9/1995 | Hansen |
| 5,470,843 A | 11/1995 | Stahl |
| 5,480,973 A | 1/1996 | Goodlad |
| 5,492,731 A * | 2/1996 | Temple ............... C08F 290/147 205/198 |
| 5,492,756 A | 2/1996 | Seale |
| 5,498,662 A | 3/1996 | Tanaka |
| 5,503,920 A | 4/1996 | Alkire |
| 5,534,612 A | 7/1996 | Taylor |
| 5,536,766 A | 7/1996 | Seyffer |
| 5,538,783 A | 7/1996 | Hansen |
| 5,543,215 A | 8/1996 | Hansen |
| 5,545,279 A | 8/1996 | Hall |
| 5,547,541 A | 8/1996 | Hansen |
| 5,547,745 A | 8/1996 | Hansen |
| 5,550,189 A | 8/1996 | Qin |
| 5,554,730 A | 9/1996 | Woiszwillo |
| 5,562,740 A | 10/1996 | Cook |
| 5,571,618 A | 11/1996 | Hansen |
| 5,578,678 A | 11/1996 | Hartmann |
| 5,580,856 A | 12/1996 | Prestrelski |
| 5,582,682 A | 12/1996 | Ferretti |
| 5,583,193 A | 12/1996 | Aravindakshan |
| 5,589,256 A | 12/1996 | Hansen |
| 5,589,536 A | 12/1996 | Golino |
| 5,607,759 A | 3/1997 | Hansen |
| 5,608,011 A | 3/1997 | Eck |
| 5,609,727 A | 3/1997 | Hansen |
| 5,614,570 A | 3/1997 | Hansen |
| 5,620,940 A | 4/1997 | Birbara |
| 5,621,026 A | 4/1997 | Tanaka |
| 5,633,298 A | 5/1997 | Arfaei |
| 5,641,561 A | 6/1997 | Hansen |
| 5,643,978 A | 7/1997 | Darwin |
| 5,645,756 A | 7/1997 | Dubin |
| 5,660,904 A | 8/1997 | Andersen |
| 5,661,213 A | 8/1997 | Arkens |
| 5,670,585 A | 9/1997 | Taylor |
| 5,672,418 A | 9/1997 | Hansen |
| 5,672,659 A | 9/1997 | Shalaby |
| 5,690,715 A | 11/1997 | Schiwek |
| 5,691,060 A | 11/1997 | Levy |
| 5,693,411 A | 12/1997 | Hansen |
| 5,719,092 A | 2/1998 | Arrington |
| 5,719,228 A | 2/1998 | Taylor |
| 5,733,624 A | 3/1998 | Syme |
| 5,756,580 A | 5/1998 | Natori |
| 5,763,524 A | 6/1998 | Arkens |
| 5,788,243 A | 8/1998 | Harshaw |
| 5,788,423 A | 8/1998 | Perkins |
| 5,807,364 A | 9/1998 | Hansen |
| 5,855,987 A | 1/1999 | Margel |
| 5,863,985 A | 1/1999 | Shalaby |
| 5,885,337 A | 3/1999 | Nohr |
| 5,895,804 A | 4/1999 | Lee |
| 5,905,115 A | 5/1999 | Luitjes |
| 5,916,503 A | 6/1999 | Rettenbacher |
| 5,919,528 A | 7/1999 | Huijs |
| 5,919,831 A | 7/1999 | Philipp |
| 5,922,403 A | 7/1999 | Tecle |
| 5,925,722 A | 7/1999 | Exner |
| 5,929,184 A | 7/1999 | Holmes-Farley |
| 5,929,196 A | 7/1999 | Kissel |
| 5,932,344 A | 8/1999 | Ikemoto |
| 5,932,665 A | 8/1999 | Deporter |
| 5,932,689 A | 8/1999 | Arkens |
| 5,942,123 A | 8/1999 | McArdle |
| 5,954,869 A | 9/1999 | Elfersy |
| 5,977,224 A | 11/1999 | Cheung |
| 5,977,232 A | 11/1999 | Arkens |
| 5,981,719 A | 11/1999 | Woiszwillo |
| 5,983,586 A | 11/1999 | Berdan, II |
| 5,990,216 A | 11/1999 | Cai |
| 5,993,709 A | 11/1999 | Bonomo |
| 6,022,615 A | 2/2000 | Rettenbacher |
| 6,067,821 A | 5/2000 | Jackson |
| 6,071,549 A | 6/2000 | Hansen |
| 6,071,994 A | 6/2000 | Hummerich |
| 6,072,086 A | 6/2000 | James |
| 6,077,883 A | 6/2000 | Taylor |
| 6,090,925 A | 7/2000 | Woiszwillo |
| 6,114,033 A | 9/2000 | Ikemoto |
| 6,114,464 A | 9/2000 | Reck |
| 6,133,347 A | 10/2000 | Vickers, Jr. |
| 6,136,916 A | 10/2000 | Arkens |
| 6,139,619 A | 10/2000 | Zaretskiy |
| 6,143,243 A | 11/2000 | Gershun |
| 6,171,444 B1 | 1/2001 | Nigam |
| 6,171,654 B1 | 1/2001 | Salsman |
| 6,180,037 B1 | 1/2001 | Andersen |
| 6,194,512 B1 | 2/2001 | Chen |
| 6,210,472 B1 | 4/2001 | Kwan |
| 6,221,958 B1 | 4/2001 | Shalaby |
| 6,221,973 B1 | 4/2001 | Arkens |
| 6,231,721 B1 | 5/2001 | Quick |
| 6,274,661 B1 | 8/2001 | Chen |
| 6,281,298 B1 | 8/2001 | Papsin, Jr. |
| 6,299,677 B1 | 10/2001 | Johnson |
| 6,299,936 B1 | 10/2001 | Reck |
| 6,307,732 B1 | 10/2001 | Tsubaki |
| 6,310,227 B1 | 10/2001 | Sarama |
| 6,313,102 B1 | 11/2001 | Colaco |
| 6,319,683 B1 | 11/2001 | James |
| 6,331,350 B1 | 12/2001 | Taylor |
| 6,331,513 B1 | 12/2001 | Zaid |
| 6,340,411 B1 | 1/2002 | Hansen |
| 6,348,530 B1 | 2/2002 | Reck |
| 6,365,079 B1 * | 4/2002 | Winkler et al. ............... 264/143 |
| 6,372,077 B1 | 4/2002 | Tecle |
| 6,379,739 B1 | 4/2002 | Formanek |
| 6,379,814 B1 | 4/2002 | Dupre |
| 6,395,856 B1 | 5/2002 | Petty |
| 6,403,665 B1 | 6/2002 | Sieker |
| 6,407,225 B1 * | 6/2002 | Mang et al. ............... 536/123.1 |
| 6,410,036 B1 | 6/2002 | De Rosa |
| 6,440,204 B1 | 8/2002 | Rogols |
| 6,441,122 B1 | 8/2002 | DeMott |
| 6,461,553 B1 | 10/2002 | Hansen |
| 6,468,442 B2 | 10/2002 | Bytnar |
| 6,468,730 B2 | 10/2002 | Fujiwara |
| 6,469,120 B1 | 10/2002 | Elfersy |
| 6,475,552 B1 | 11/2002 | Shah |
| 6,482,875 B2 | 11/2002 | Lorenz |
| 6,495,656 B1 | 12/2002 | Haile |
| 6,521,339 B1 | 2/2003 | Hansen |
| 6,525,009 B2 | 2/2003 | Sachdev |
| 6,538,057 B1 | 3/2003 | Wildburg |
| 6,547,867 B2 | 4/2003 | Rogols |
| 6,555,616 B1 | 4/2003 | Helbing |
| 6,559,302 B1 | 5/2003 | Shah |
| 6,562,267 B1 | 5/2003 | Hansen |
| 6,596,103 B1 | 7/2003 | Hansen |
| 6,613,378 B1 | 9/2003 | Erhan |
| 6,638,882 B1 | 10/2003 | Helbing |
| 6,638,884 B2 | 10/2003 | Quick |
| 6,699,945 B1 | 3/2004 | Chen |
| 6,706,853 B1 | 3/2004 | Stanssens |
| 6,719,862 B2 | 4/2004 | Quick |
| 6,730,730 B1 | 5/2004 | Hansen |
| 6,753,361 B2 | 6/2004 | Kroner |
| 6,818,694 B2 | 11/2004 | Hindi |
| 6,821,547 B2 | 11/2004 | Shah |
| 6,852,247 B2 | 2/2005 | Bytnar |
| 6,858,074 B2 | 2/2005 | Anderson |
| 6,861,495 B2 | 3/2005 | Barsotti |
| 6,864,044 B2 | 3/2005 | Ishikawa |

(56) References Cited

U.S. PATENT DOCUMENTS

| | | |
|---|---|---|
| 6,878,800 B2 | 4/2005 | Husemoen |
| 6,884,849 B2 | 4/2005 | Chen |
| 6,955,844 B2 | 10/2005 | Tagge |
| 6,962,714 B2 | 11/2005 | Hei |
| 6,989,171 B2 | 1/2006 | Portman |
| 6,992,203 B2 | 1/2006 | Trusovs |
| 7,018,490 B2 | 3/2006 | Hansen |
| 7,029,717 B1 | 4/2006 | Ojima |
| 7,067,579 B2 | 6/2006 | Taylor |
| 7,083,831 B1 | 8/2006 | Koch |
| 7,090,745 B2 | 8/2006 | Beckman |
| 7,141,626 B2 | 11/2006 | Rodrigues |
| 7,144,474 B1 | 12/2006 | Hansen |
| 7,195,792 B2 | 3/2007 | Boston |
| 7,201,778 B2 | 4/2007 | Smith |
| 7,201,825 B2 | 4/2007 | Dezutter |
| 7,202,326 B2 | 4/2007 | Kuroda |
| 7,241,487 B2 | 7/2007 | Taylor |
| 7,458,235 B2 | 12/2008 | Beaufils |
| 7,514,027 B2 | 4/2009 | Horres |
| 7,655,711 B2 | 2/2010 | Swift |
| 7,772,347 B2 | 8/2010 | Swift |
| 7,795,354 B2 | 9/2010 | Srinivasan |
| 7,803,879 B2 | 9/2010 | Srinivasan |
| 7,807,771 B2 | 10/2010 | Swift |
| 7,842,382 B2 | 11/2010 | Helbing |
| 7,854,980 B2 | 12/2010 | Jackson |
| D631,670 S * | 2/2011 | Jackson .................... D5/99 |
| 7,883,693 B2 * | 2/2011 | Sehl et al. ............... 424/78.03 |
| 7,888,445 B2 | 2/2011 | Swift |
| 7,947,765 B2 | 5/2011 | Swift |
| 8,114,210 B2 | 2/2012 | Hampson |
| 8,182,648 B2 | 5/2012 | Swift |
| 8,211,923 B2 | 7/2012 | Wagner |
| 8,372,900 B2 | 2/2013 | Shooshtari |
| 8,377,564 B2 | 2/2013 | Shooshtari |
| 8,501,838 B2 | 8/2013 | Jackson |
| 8,680,224 B2 | 3/2014 | Zhang |
| 8,691,934 B2 | 4/2014 | Helbing |
| 8,900,495 B2 | 12/2014 | Pacorel |
| 9,493,603 B2 * | 11/2016 | Mueller .................. C08G 12/00 |
| 2001/0017427 A1 | 8/2001 | Rosthauser |
| 2001/0046824 A1 | 11/2001 | Nigam |
| 2002/0000100 A1 | 1/2002 | Burg |
| 2002/0025435 A1 | 2/2002 | Hansen |
| 2002/0026025 A1 | 2/2002 | Kuo |
| 2002/0028857 A1 * | 3/2002 | Holy ........................ 523/124 |
| 2002/0032253 A1 | 3/2002 | Lorenz |
| 2002/0042473 A1 | 4/2002 | Trollsas |
| 2002/0091185 A1 | 7/2002 | Taylor |
| 2002/0096278 A1 | 7/2002 | Foster |
| 2002/0123598 A1 | 9/2002 | Sieker |
| 2002/0130439 A1 | 9/2002 | Kroner |
| 2002/0161108 A1 | 10/2002 | Schultz |
| 2002/0197352 A1 | 12/2002 | Portman |
| 2003/0005857 A1 | 1/2003 | Minami |
| 2003/0040239 A1 | 2/2003 | Toas |
| 2003/0044513 A1 | 3/2003 | Shah |
| 2003/0066523 A1 | 4/2003 | Lewis |
| 2003/0071879 A1 | 4/2003 | Swenson |
| 2003/0116294 A1 | 6/2003 | Kehrer |
| 2003/0134945 A1 | 7/2003 | Capps |
| 2003/0148084 A1 | 8/2003 | Trocino |
| 2003/0153690 A1 | 8/2003 | Husemoen |
| 2003/0185991 A1 | 10/2003 | Wigger |
| 2003/0203117 A1 | 10/2003 | Bartkowiak |
| 2004/0002567 A1 | 1/2004 | Chen |
| 2004/0019168 A1 | 1/2004 | Soerens |
| 2004/0024170 A1 | 2/2004 | Husemoen |
| 2004/0033269 A1 | 2/2004 | Hei |
| 2004/0033747 A1 | 2/2004 | Miller |
| 2004/0034154 A1 | 2/2004 | Tutin |
| 2004/0038017 A1 | 2/2004 | Tutin |
| 2004/0048531 A1 | 3/2004 | Belmares |
| 2004/0077055 A1 | 4/2004 | Fosdick |
| 2004/0079499 A1 | 4/2004 | Dezutter |
| 2004/0087024 A1 | 5/2004 | Bellocq |
| 2004/0087719 A1 | 5/2004 | Rautschek |
| 2004/0122166 A1 | 6/2004 | O'Brien-Bernini |
| 2004/0131874 A1 | 7/2004 | Tutin |
| 2004/0144706 A1 | 7/2004 | Beaufils |
| 2004/0152824 A1 | 8/2004 | Dobrowolski |
| 2004/0161993 A1 | 8/2004 | Tripp |
| 2004/0209851 A1 | 10/2004 | Nelson |
| 2004/0213930 A1 | 10/2004 | Halabisky |
| 2004/0220368 A1 | 11/2004 | Li |
| 2004/0249066 A1 | 12/2004 | Heinzman |
| 2004/0254285 A1 | 12/2004 | Rodrigues |
| 2004/0260082 A1 | 12/2004 | Van Der Wilden |
| 2005/0001198 A1 | 1/2005 | Bytnar |
| 2005/0017394 A1 | 1/2005 | Hochsmann |
| 2005/0027283 A1 | 2/2005 | Richard |
| 2005/0033037 A1 | 2/2005 | Trusovs |
| 2005/0048212 A1 | 3/2005 | Clamen |
| 2005/0059770 A1 | 3/2005 | Srinivasan |
| 2005/0171085 A1 | 8/2005 | Pinto |
| 2005/0196421 A1 | 9/2005 | Hunter |
| 2005/0202224 A1 | 9/2005 | Helbing |
| 2005/0208852 A1 | 9/2005 | Weber |
| 2005/0215153 A1 | 9/2005 | Cossement |
| 2005/0245669 A1 | 11/2005 | Clungeon |
| 2005/0275133 A1 | 12/2005 | Cabell |
| 2005/0288479 A1 | 12/2005 | Kuroda |
| 2006/0005580 A1 | 1/2006 | Espiard |
| 2006/0009569 A1 | 1/2006 | Charbonneau |
| 2006/0044302 A1 | 3/2006 | Chen |
| 2006/0099870 A1 | 5/2006 | Garcia |
| 2006/0111480 A1 | 5/2006 | Hansen |
| 2006/0124538 A1 | 6/2006 | Morcrette |
| 2006/0135433 A1 | 6/2006 | Murray |
| 2006/0141177 A1 | 6/2006 | Ligtenberg |
| 2006/0179892 A1 | 8/2006 | Horres |
| 2006/0188465 A1 | 8/2006 | Perrier |
| 2006/0198954 A1 | 9/2006 | Frechem |
| 2006/0231487 A1 | 10/2006 | Bartley |
| 2006/0252855 A1 | 11/2006 | Pisanova |
| 2006/0281622 A1 | 12/2006 | Maricourt |
| 2007/0006390 A1 | 1/2007 | Clamen |
| 2007/0009582 A1 | 1/2007 | Madsen |
| 2007/0027281 A1 | 2/2007 | Michl |
| 2007/0027283 A1 * | 2/2007 | Swift .................. C07H 5/04 527/312 |
| 2007/0039520 A1 | 2/2007 | Crews |
| 2007/0082983 A1 | 4/2007 | Crews |
| 2007/0123679 A1 | 5/2007 | Swift |
| 2007/0123680 A1 | 5/2007 | Swift |
| 2007/0129522 A1 | 6/2007 | Burckhardt |
| 2007/0142596 A1 | 6/2007 | Swift |
| 2007/0158022 A1 | 7/2007 | Heep |
| 2007/0184740 A1 | 8/2007 | Keller |
| 2007/0191574 A1 | 8/2007 | Miller |
| 2007/0270070 A1 | 11/2007 | Othman |
| 2007/0287018 A1 | 12/2007 | Tutin |
| 2007/0292618 A1 | 12/2007 | Srinivasan |
| 2007/0292619 A1 | 12/2007 | Srinivasan |
| 2007/0298274 A1 | 12/2007 | Eriksson |
| 2008/0009209 A1 | 1/2008 | Clamen |
| 2008/0009616 A1 | 1/2008 | Frank |
| 2008/0051539 A1 * | 2/2008 | Kelly .................. C09D 133/08 526/199 |
| 2008/0060551 A1 * | 3/2008 | Crews et al. ................. 106/277 |
| 2008/0081138 A1 | 4/2008 | Moore |
| 2008/0108741 A1 | 5/2008 | Van Herwijnen |
| 2008/0160260 A1 | 7/2008 | Wada |
| 2008/0160302 A1 | 7/2008 | Asrar |
| 2008/0194738 A1 * | 8/2008 | Crews et al. .................... 524/60 |
| 2009/0169867 A1 * | 7/2009 | Kelly ..................... C08L 89/00 428/326 |
| 2009/0170978 A1 | 7/2009 | Kelly |
| 2009/0227732 A1 | 9/2009 | Glockner |
| 2009/0301972 A1 | 12/2009 | Hines |
| 2009/0304919 A1 | 12/2009 | Huenig |
| 2009/0306255 A1 | 12/2009 | Patel |
| 2009/0324915 A1 | 12/2009 | Swift |

(56) References Cited

U.S. PATENT DOCUMENTS

| | | | |
|---|---|---|---|
| 2010/0029160 A1 | 2/2010 | Srinivasan | |
| 2010/0058661 A1 | 3/2010 | Jackson | |
| 2010/0084976 A1 | 4/2010 | Jackson | |
| 2010/0084598 A1 | 4/2010 | Jackson | |
| 2010/0086726 A1 | 4/2010 | Jackson | |
| 2010/0087571 A1 | 4/2010 | Jackson | |
| 2010/0098947 A1 | 4/2010 | Inoue | |
| 2010/0117023 A1 | 5/2010 | Dopico | |
| 2010/0129640 A1 | 5/2010 | Kelly | |
| 2010/0130649 A1 | 5/2010 | Swift | |
| 2010/0175826 A1 | 7/2010 | Huenig | |
| 2010/0210595 A1 | 8/2010 | Wagner | |
| 2010/0222463 A1 | 9/2010 | Brady | |
| 2010/0222566 A1 | 9/2010 | Fosdick | |
| 2010/0282996 A1 | 11/2010 | Jaffrennou | |
| 2010/0301256 A1 | 12/2010 | Hampson | |
| 2010/0320113 A1 | 12/2010 | Swift | |
| 2011/0021672 A1 | 1/2011 | Crews | |
| 2011/0039111 A1 | 2/2011 | Shooshtari | |
| 2011/0040010 A1 | 2/2011 | Shooshtari | |
| 2011/0042303 A1 | 2/2011 | Shooshtari | |
| 2011/0045966 A1* | 2/2011 | Shooshtari et al. | 502/159 |
| 2011/0089074 A1 | 4/2011 | Jackson | |
| 2011/0135937 A1* | 6/2011 | Swift et al. | 428/426 |
| 2011/0190425 A1 | 8/2011 | Swift | |
| 2011/0220835 A1* | 9/2011 | Swift et al. | 252/62 |
| 2011/0256790 A1 | 10/2011 | Toas | |
| 2011/0260094 A1 | 10/2011 | Hampson | |
| 2011/0262648 A1 | 10/2011 | Lee | |
| 2011/0263757 A1 | 10/2011 | Rand | |
| 2011/0306726 A1 | 12/2011 | Bailey | |
| 2012/0133073 A1 | 5/2012 | Pacorel | |
| 2012/0156954 A1* | 6/2012 | Eckert et al. | 442/180 |
| 2013/0029150 A1 | 1/2013 | Appley | |
| 2013/0032749 A1 | 2/2013 | Jaffrennou | |
| 2013/0047888 A1 | 2/2013 | Mueller | |
| 2013/0059075 A1 | 3/2013 | Appley | |
| 2013/0082205 A1 | 4/2013 | Mueller | |
| 2013/0174758 A1 | 7/2013 | Mueller | |
| 2013/0234362 A1* | 9/2013 | Swift et al. | 264/257 |
| 2013/0236650 A1* | 9/2013 | Swift et al. | 427/379 |
| 2013/0237113 A1* | 9/2013 | Swift et al. | 442/410 |
| 2013/0244524 A1* | 9/2013 | Swift et al. | 442/327 |
| 2014/0091247 A1 | 4/2014 | Jackson | |
| 2014/0134909 A1 | 5/2014 | Guo | |
| 2014/0357787 A1 | 12/2014 | Jobber | |

FOREIGN PATENT DOCUMENTS

| | | |
|---|---|---|
| CA | 1090026 | 11/1980 |
| CA | 2037214 | 9/1991 |
| CA | 2232334 | 11/1998 |
| CA | 2458333 | 12/1999 |
| CA | 2278946 | 1/2000 |
| CA | 2470783 | 12/2004 |
| CN | 1251738 | 5/2000 |
| DE | 1905054 | 8/1969 |
| DE | 4142261 | 6/1993 |
| DE | 4233622 | 4/1994 |
| DE | 4308089 | 9/1994 |
| DE | 102004033561 | 9/2005 |
| DE | 102005023431 | 11/2006 |
| EP | 0044614 A2 | 1/1982 |
| EP | 0099801 | 2/1984 |
| EP | 354023 | 2/1990 |
| EP | 0461995 | 12/1991 |
| EP | 0524518 A2 | 1/1993 |
| EP | 0547819 A2 | 6/1993 |
| EP | 0583086 A1 | 2/1994 |
| EP | 0714754 A2 | 6/1996 |
| EP | 796681 | 9/1997 |
| EP | 0826710 A2 | 3/1998 |
| EP | 856494 | 8/1998 |
| EP | 0873976 A1 | 10/1998 |
| EP | 878135 | 11/1998 |
| EP | 0882756 A2 | 12/1998 |
| EP | 0911361 A1 | 4/1999 |
| EP | 915811 | 5/1999 |
| EP | 936060 | 8/1999 |
| EP | 976866 | 2/2000 |
| EP | 0990729 A1 | 4/2000 |
| EP | 1038433 A1 | 9/2000 |
| EP | 1193288 A1 | 4/2002 |
| EP | 1084167 | 9/2002 |
| EP | 1268702 | 1/2003 |
| EP | 1382642 | 1/2004 |
| EP | 1486547 A2 | 12/2004 |
| EP | 1522642 | 4/2005 |
| EP | 1698598 A1 | 9/2006 |
| EP | 1767566 | 4/2007 |
| EP | 2223941 | 9/2010 |
| EP | 2253663 | 11/2010 |
| FR | 2614388 | 10/1988 |
| GB | 770561 | 3/1957 |
| GB | 809675 | 3/1959 |
| GB | 926749 | 5/1963 |
| GB | 1391172 | 4/1975 |
| GB | 1469331 | 4/1977 |
| GB | 1512066 | 5/1978 |
| GB | 1525541 | 9/1978 |
| GB | 2047258 | 11/1980 |
| GB | 2078805 A | 1/1982 |
| GB | 2173523 | 10/1986 |
| GB | 2251438 | 7/1992 |
| JP | 53113784 | 10/1978 |
| JP | 57101100 | 6/1982 |
| JP | 5811193 | 1/1983 |
| JP | 61195647 | 8/1986 |
| JP | 3-173680 | 7/1991 |
| JP | 05186635 | 7/1993 |
| JP | 7-034023 | 2/1995 |
| JP | 09157627 | 6/1997 |
| JP | 10234314 | 9/1998 |
| JP | 11035491 | 2/1999 |
| JP | 11181690 | 7/1999 |
| JP | 2000327841 | 11/2000 |
| JP | 2002293576 | 9/2002 |
| JP | 2003147276 | 5/2003 |
| JP | 2003238921 | 8/2003 |
| JP | 2004060058 | 2/2004 |
| JP | 2005306919 | 11/2005 |
| NZ | 549563 | 1/2008 |
| RU | 1765996 | 8/1995 |
| SU | 374400 | 3/1973 |
| WO | 1990007541 | 7/1990 |
| WO | 1992012198 | 7/1992 |
| WO | 1995034517 | 12/1995 |
| WO | 1997049646 | 12/1997 |
| WO | 1999036368 | 7/1999 |
| WO | 199947765 | 9/1999 |
| WO | 199960042 | 11/1999 |
| WO | 199960043 | 11/1999 |
| WO | 200058085 | 10/2000 |
| WO | 2001014491 | 3/2001 |
| WO | 2001059026 | 8/2001 |
| WO | 200200429 | 1/2002 |
| WO | 200206178 | 1/2002 |
| WO | 2003029496 | 4/2003 |
| WO | 2003071879 | 9/2003 |
| WO | 2003106561 | 12/2003 |
| WO | 2004007615 | 1/2004 |
| WO | 2004076734 | 9/2004 |
| WO | 2005087837 | 9/2005 |
| WO | 2006044302 | 4/2006 |
| WO | 2006136614 | 12/2006 |
| WO | 2007014236 | 2/2007 |
| WO | 2007024020 A1 | 3/2007 |
| WO | 2007050964 | 5/2007 |
| WO | 2007112335 | 10/2007 |
| WO | 2008089847 | 7/2008 |
| WO | 2008089851 | 7/2008 |
| WO | 2008141201 | 11/2008 |
| WO | 2009019235 | 2/2009 |
| WO | 2009129084 | 10/2009 |

(56) References Cited

FOREIGN PATENT DOCUMENTS

| | | |
|---|---|---|
| WO | 2010027937 | 3/2010 |
| WO | 2010139899 | 12/2010 |
| WO | 2011019590 | 2/2011 |
| WO | 2011019593 | 2/2011 |
| WO | 2011019597 | 2/2011 |
| WO | 2011019598 | 2/2011 |
| WO | 2011022224 | 2/2011 |
| WO | 2011022226 | 2/2011 |
| WO | 2011022227 | 2/2011 |
| WO | 2011138458 | 11/2011 |
| WO | 2011138459 | 11/2011 |
| WO | 2013150123 | 10/2013 |

OTHER PUBLICATIONS

16425301 Example 1 calculations (Year: 2018).*
International Search Report and Written Opinion for PCT/US2008/059730, completed Sep. 22, 2008.
International Search Report and Written Opinion for PCT/US2008/069046, completed Sep. 25, 2008.
International Search Report and Written Opinion for PCT/EP2011/057364, completed Sep. 5, 2011.
International Search Report and Written Opinion for PCT/EP2011/059317, completed Jul. 15, 2011.
International Search Report for PCT/EP2008/060185, completed Oct. 23, 2008.
International Search Report for PCT/EP2011/057363, completed Sep. 5, 2011.
Ames, J.M., "The Maillard Browning Reaction—an Update, "Chemistry & Industry, No. 17, 1988, 4 pages.
"Gamma-aminopropyltrimethoxysilane,"Hawley'S Condensed Chemical Dictionary, 14th Edition, John Wiley & Sons, Inc., 2002, 1 page.
Hodge, J.E., Chemistry of Browning Reactions in Model Systems, 1953, J. Agric. Food Chem., vol. 1, No. 15, pp. 928-943.
Agyei-Aye et al., "The Role of Anion in the Reaction of Reducing Sugars with Ammonium Salts," Carbohydrate Research 2002, 337: 2273-2277.
Laroque et al., "Kinetic study on the Maillard reaction. Consideration of sugar reactivity," Food Chemistry 2008, 111: 1032-1042.
Bjorksten et al., "Polyester Resin—Glass Fiber Laminates," Industrial and Engineering Chemistry (1954).
Dow Corning, "A Guide to Silane Solutions," 2005.
Knauf Data Sheet, 2006.
Molasses Corporation, United States Sugar Corporation, http://www.suga-lik.com/molasses/composition.html (Sep. 29, 2003).
Clamen, Guy, "Acrylic Thermosets: A Safe Alternative to Formaldehyde Resins," Nonwovens World, Apr.-May 2004, pp. 96-102.
Opposition to AU 2006272595, Amended Statement of Grounds and Particulars, issued from Australian Patent Office, Jul. 6, 2012, 22 pages.
Decision re Opposition to AU 2006272595, issued from Australian Patent Office, Aug. 14, 2015, 25 pages.
Opposition to EP 1732968, Notice of Opposition: Prior Art, Scope of the Patent, Reasons for the Opposition, issued from European Patent Office, Mar. 8, 2012, 18 pages.
Decision re Opposition to EP 1732968, issued from the European Patent Office, Nov. 14, 2014, 5 pages.
Opposition to EA 019802, submitted to Eurasian Patent Office on Dec. 26, 2014, 36 pages.
Decision re Opposition to EA 019802, issued by Eurasian Patent Office on Aug. 18, 2015, 15 pages.
Owens Corning Retiree Update: What Goes Around, Comes Around: A tale of Natural Binders, revised Mar. 20, 2013 p. 4.
A.P. Bryant, "The Terminology of Sugars," Industrial and Engineering Chemistry, vol. 26, No. 2, p. 231, Feb. 1934.
Food Flavor Chemistry, p. 162, Mar. 21, 2009 (English Abstract).
Viswanathan, T., "Chapter 28: Thermosetting Adhesive Resins from Whey and Whey Byproducts," in Adhesives from Renewable Resources, ACS Symposium Series, Hemingway, R.W., et al. (Eds.), American Chemical Society, Washington, DC (1989).
Viswanathan, T., and Richardson, T., "Thermosetting Adhesive Resins from Whey and Whey Byproducts," Ind. Eng. Chem. Prod. Res. Dev. 23:644-47, American Chemical Society, United States (1984).
Residential Energy Conservation: vol. 1, Congress of the U.S., Office of Technology Assessment (Ed.), 357 pages (Jan. 1, 1979).
Office action for co-pending U.S. Appl. No. 12/524,502 (9 pages)—dated Sep. 21, 2012.
Office action for co-pending U.S. Appl. No. 12/524,502 (9 pages)—dated Apr. 4, 2013.
Office action for co-pending U.S. Appl. No. 12/524,512 (7 pages)—dated Aug. 6, 2012.
Office action for co-pending U.S. Appl. No. 12/524,512 (9 pages)—dated Apr. 1, 2013.
Office action for co-pending U.S. Appl. No. 12/524,512 (14 pages)—dated Nov. 12, 2014.
Office action for co-pending U.S. Appl. No. 12/524,512 (9 pages)—dated Jul. 10, 2015.
Office action for co-pending U.S. Appl. No. 12/524,512 (10 pages)—dated Mar. 23, 2016.
Office action for co-pending U.S. Appl. No. 12/524,512 (13 pages)—dated Oct. 5, 2016.
Office action for co-pending U.S. Appl. No. 12/524,512 (13 pages)—dated Apr. 6, 2018.
Office action for co-pending U.S. Appl. No. 12/524,512 (15 pages)—dated Jan. 17, 2019.
Office action for co-pending U.S. Appl. No. 12/524,469 (7 pages)—dated Jun. 7, 2012.
Office action for co-pending U.S. Appl. No. 12/524,469 (8 pages)—dated Jan. 29, 2013.
Office action for co-pending U.S. Appl. No. 12/524,469 (7 pages)—dated Aug. 20, 2013.
Office action for co-pending U.S. Appl. No. 12/524,469 (9 pages)—dated Jun. 9, 2014.
Office action for co-pending U.S. Appl. No. 12/524,469 (9 pages)—dated Oct. 17, 2014.
Office action for co-pending U.S. Appl. No. 12/524,469 (9 pages)—dated Jul. 23, 2015.
Office action for co-pending U.S. Appl. No. 12/524,539 (13 pages)—dated Jun. 21, 2012.
Office action for co-pending U.S. Appl. No. 12/524,539 (13 pages)—dated Jun. 6, 2013.
Office action for co-pending U.S. Appl. No. 12/524,539 (12 pages)—dated Dec. 17, 2014.
Office action for co-pending U.S. Appl. No. 12/524,539 (7 pages)—dated Jul. 15, 2015.
Office action for co-pending U.S. Appl. No. 12/524,539 (7 pages)—dated Mar. 23, 2016.
Office action for co-pending U.S. Appl. No. 12/524,539 (7 pages)—dated Dec. 29, 2016.
Office action for co-pending U.S. Appl. No. 12/524,522 (4 pages)—dated Oct. 11, 2011.
Office action for co-pending U.S. Appl. No. 12/667,718 (5 pages)—dated Sep. 3, 2013.
Office action for co-pending U.S. Appl. No. 12/667,718 (6 pages)—dated Sep. 9, 2014.
Office action for co-pending U.S. Appl. No. 12/671,922 (10 pages)—dated Oct. 7, 2011.
Office action for co-pending U.S. Appl. No. 12/671,922 (10 pages)—dated May 10, 2012.
Office action for co-pending U.S. Appl. No. 12/671,922 (9 pages)—dated Sep. 23, 2014.
Office action for co-pending U.S. Appl. No. 12/671,922 (5 pages)—dated Apr. 4, 2016.
Office action for co-pending U.S. Appl. No. 13/388,408 (5 pages)—dated Aug. 15, 2013.
Office action for co-pending U.S. Appl. No. 13/371,829 (9 pages)—dated Dec. 20, 2012.
Office action for co-pending U.S. Appl. No. 13/371,829 (6 pages)—dated Jul. 12, 2013.

(56) References Cited

OTHER PUBLICATIONS

Office action for co-pending U.S. Appl. No. 13/371,829 (6 pages)—dated Aug. 12, 2014.
Office action for co-pending U.S. Appl. No. 13/637,794 (8 pages)—dated Aug. 12, 2013.
Office action for co-pending U.S. Appl. No. 13/637,794 (9 pages)—dated Mar. 26, 2014.
Office action for co-pending U.S. Appl. No. 13/696,439 (11 pages)—dated Jan. 8, 2014.
Office action for co-pending U.S. Appl. No. 13/696,452 (7 pages)—dated Jan. 13, 2015.
Office action for co-pending U.S. Appl. No. 13/696,452 (9 pages)—dated Oct. 27, 2015.
Office action for co-pending U.S. Appl. No. 13/702,144 (6 pages)—dated Jan. 10, 2014.
Office action for co-pending U.S. Appl. No. 13/702,144 (7 pages)—dated Jul. 29, 2014.
Office action for co-pending U.S. Appl. No. 13/823,818 (9 pages)—dated Mar. 26, 2015.
Office action for co-pending U.S. Appl. No. 13/866,368 (16 pages)—dated Aug. 29, 2013.
Office action for co-pending U.S. Appl. No. 13/866,368 (11 pages)—dated Apr. 16, 2014.
Office action for co-pending U.S. Appl. No. 13/866,368 (8 pages)—dated Aug. 21, 2014.
Office action for co-pending U.S. Appl. No. 13/866,419 (14 pages)—dated Sep. 20, 2013.
Office action for co-pending U.S. Appl. No. 13/866,419 (10 pages)—dated Apr. 25, 2014.
Office action for co-pending U.S. Appl. No. 13/866,419 (8 pages)—dated Oct. 9, 2014.
Office action for co-pending U.S. Appl. No. 13/866,419 (8 pages)—dated Sep. 25, 2015.
Office action for co-pending U.S. Appl. No. 13/868,233 (23 pages)—dated Aug. 13, 2013.
Office action for co-pending U.S. Appl. No. 13/868,233 (12 pages)—dated Apr. 15, 2014.
Office action for co-pending U.S. Appl. No. 13/868,233 (8 pages)—dated Oct. 7, 2014.
Office action for co-pending U.S. Appl. No. 13/868,233 (8 pages)—dated Jul. 16, 2015.
Office action for co-pending U.S. Appl. No. 13/868,238 (8 pages)—dated Jul. 16, 2014.
Office action for co-pending U.S. Appl. No. 12/976,379 (7 pages)—dated Jan. 10, 2012.
Office action for co-pending U.S. Appl. No. 12/976,379 (6 pages)—dated Jul. 27, 2012.
Office action for co-pending U.S. Appl. No. 12/976,379 (9 pages)—dated Mar. 7, 2013.
Office action for co-pending U.S. Appl. No. 12/976,379 (8 pages)—dated Aug. 20, 2013.
Office action for co-pending U.S. Appl. No. 12/599,858 (8 pages)—dated May 11, 2011.
Office action for co-pending U.S. Appl. No. 13/341,542 (8 pages)—dated Dec. 26, 2012.
Office action for co-pending U.S. Appl. No. 13/341,542 (7 pages)—dated Feb. 10, 2014.
Office action for co-pending U.S. Appl. No. 14/026,394 (6 pages)—dated Aug. 14, 2014.
Office action for co-pending U.S. Appl. No. 14/272,556 (14 pages)—dated Nov. 20, 2014.
Office action for co-pending U.S. Appl. No. 14/272,556 (12 pages)—dated Sep. 17, 2015.
Office action for co-pending U.S. Appl. No. 14/342,069 (17 pages)—dated Dec. 29, 2015.
Office action for co-pending U.S. Appl. No. 14/342,069 (22 pages)—dated Sep. 2, 2016.
Office action for co-pending U.S. Appl. No. 14/342,069 (21 pages)—dated Sep. 26, 2017.
Office action for co-pending U.S. Appl. No. 14/342,069 (21 pages)—dated Jun. 6, 2018.
Office action for co-pending U.S. Appl. No. 14/649,277 (9 pages)—dated Jul. 22, 2016.
Office action for co-pending U.S. Appl. No. 14/686,915 (8 pages)—dated Nov. 18, 2016.
Office action for co-pending U.S. Appl. No. 14/810,765 (7 pages)—dated Jan. 29, 2016.
Office action for co-pending U.S. Appl. No. 14/828,916 (8 pages)—dated Nov. 25, 2016.
Office action for co-pending U.S. Appl. No. 14/867,502 (9 pages)—dated Nov. 18, 2016.
Office action for co-pending U.S. Appl. No. 15/172,432 (16 pages)—dated Apr. 17, 2017.
Office action for co-pending U.S. Appl. No. 15/702,087 (5 pages)—dated Nov. 9, 2018.
Office action for co-pending U.S. Appl. No. 15/177,442 (17 pages)—dated May 19, 2017.
Office action for co-pending U.S. Appl. No. 15/378,159 (18 pages)—dated Mar. 2, 2017.
Office action for co-pending U.S. Appl. No. 15/222,122 (8 pages)—dated Nov. 20, 2017.
Office action for co-pending U.S. Appl. No. 15/310,837 (13 pages)—dated Jun. 21, 2018.
Office action for co-pending U.S. Appl. No. 15/411,972 (9 pages)—dated Mar. 28, 2017.
Office action for co-pending U.S. Appl. No. 15/411,972 (8 pages)—dated Nov. 29, 2017.
Office action for co-pending U.S. Appl. No. 15/411,972 (9 pages)—dated Jun. 14, 2018.
Office action for co-pending U.S. Appl. No. 15/116,254 (8 pages)—dated Apr. 26, 2018.
Office action for co-pending U.S. Appl. No. 15/116,254 (10 pages)—dated Aug. 15, 2018.
Office action for co-pending U.S. Appl. No. 15/333,670 (5 pages)—dated Dec. 8, 2017.
Office Action for co-pending U.S. Appl. No. 14/116,048 (10 pages)—dated Jun. 23, 2017.
Office action for co-pending U.S. Appl. No. 15/959,131 (8 pages)—dated Nov. 8, 2019.
Office action for co-pending U.S. Appl. No. 15/822,102 (6 pages)—dated Dec. 6, 2019.
Office action for co-pending U.S. Appl. No. 15/690,623 (6 pages)—dated Jan. 9, 2020.
Other Information—Narrative of verbal disclosure of Brian Swift (1 page)—May 13, 2014.
Petition for Inter Partes Review of U.S. Pat. No. 8,114,210 (52 pages, filed Jun. 12, 2015 by Petitioners Johns Manville Corporation and Johns Manville, Inc.).
Declaration of Dr. Frederick J. Hirsekorn Regarding U.S. Pat. No. 8,114,210 (58 pages, filed Jun. 12, 2015 by Petitioners Johns Manville Corporation and Johns Manville, Inc. in connection with Petition for Inter Partes Review of U.S. Pat. No. 8,114,210).
1st Petition for Inter Partes Review of U.S. Patent No. D631,670 (68 pages, filed Jun. 19, 2015 by Petitioners Johns Manville Corporation and Johns Manville, Inc.).
2nd Petition for Inter Partes Review of U.S. Patent No. D631,670 (62 pages, filed Nov. 2, 2015 by Petitioners Johns Manville Corporation and Johns Manville, Inc.).
Decision of PTAB regarding Institution of Inter Partes Review for U.S. Patent No. D631,670 (33 pages)—Jan. 12, 2016.
Decision of PTAB regarding Institution of Inter Partes Review for U.S. Patent No. D631,670 (27 pages)—May 9, 2016.
Final Written Decision of PTAB regarding Inter Partes Review of D631,670 based on 1st Petition (56 pages)—Jan. 11, 2017.
Final Written Decision of PTAB regarding Inter Partes Review of D631,670 based on 2nd Petition (55 pages)—dated May 8, 2017.
Court of Appeals for Federal Circuit Judgment from Appeal of PTAB Decisions in Inter Partes Reviews of U.S. Patent No. D631,670 (2 pages)—Jul. 13, 2018.
1st Petition for Inter Partes Review of U.S. Pat. No. 8,940,089 (61 pages, filed Jul. 1, 2015 by Petitioners Johns Manville Corporation and Johns Manville, Inc.).

(56) References Cited

OTHER PUBLICATIONS

Declaration of Dr. Frederick J. Hirsekorn Regarding U.S. Pat. No. 8,940,089 (70 pages, filed Jul. 1, 2015 by Petitioners Johns Manville Corporation and Johns Manville, Inc. in connection with 1st Petition for Inter Partes Review of U.S. Pat. No. 8,940,089).
2nd Petition for Inter Partes Review of U.S. Pat. No. 8,940,089 (56 pages, filed Jul. 10, 2015 by Petitioners Johns Manville Corporation and Johns Manville, Inc.).
Declaration of Dr. Frederick J. Hirsekorn Regarding U.S. Pat. No. 8,940,089 (67 pages, filed Jul. 10, 2015 by Petitioners Johns Manville Corporation and Johns Manville, Inc. in connection with 2nd Petition for Inter Partes Review of U.S. Pat. No. 8,940,089).
3rd Petition for Inter Partes Review of U.S. Pat. No. 8,940,089 (62 pages, filed Jul. 17, 2015 by Petitioners Johns Manville Corporation and Johns Manville, Inc.).
Declaration of Dr. Frederick J. Hirsekorn Regarding U.S. Pat. No. 8,940,089 (76 pages, filed Jul. 17, 2015 by Petitioners Johns Manville Corporation and Johns Manville, Inc. in connection with 3rd Petition for Inter Partes Review of U.S. Pat. No. 8,940,089).
Declaration of Dr. Elam Leed (11 pages, filed Jul. 1, Jul. 10, and Jul. 17, 2015 by Petitioners Johns Manville Corporation and Johns Manville, Inc. in connection with 1st, 2nd and 3rd Petition for Inter Partes Review of U.S. Pat. No. 8,940,089, respectively).
Declaration of Dr. Jonathan Vickers (10 pages, filed Jul. 1, Jul. 10, and Jul. 17, 2015 by Petitioners Johns Manville Corporation and Johns Manville, Inc. in connection with 1st, 2nd and 3rd Petition for Inter Partes Review of U.S. Pat. No. 8,940,089, respectively).
1st Petition for Inter Partes Review of U.S. Pat. No. 9,039,827 (60 pages, filed Jul. 29, 2015 by Petitioners Johns Manville Corporation and Johns Manville, Inc.).
Declaration of Dr. Frederick J. Hirsekorn Regarding U.S. Pat. No. 9,039,827 (72 pages, filed Jul. 29, 2015 by Petitioners Johns Manville Corporation and Johns Manville, Inc. in connection with $1^{st}$ Petition for Inter Partes Review of U.S. Pat. No. 9,039,827).
2nd Petition for Inter Partes Review of U.S. Pat. No. 9,039,827 (51 pages, filed Aug. 5, 2015 by Petitioners Johns Manville Corporation and Johns Manville, Inc.).
Declaration of Dr. Frederick J. Hirsekorn Regarding U.S. Pat. No. 9,039,827 (65 pages, filed Aug. 5, 2015 by Petitioners Johns Manville Corporation and Johns Manville, Inc. in connection with $2^{nd}$ Petition for Inter Partes Review of U.S. Pat. No. 9,039,827).
3rd Petition for Inter Partes Review of U.S. Pat. No. 9,039,827 (57 pages, filed Aug. 7, 2015 by Petitioners Johns Manville Corporation and Johns Manville, Inc.).
Declaration of Dr. Frederick J. Hirsekorn Regarding U.S. Pat. No. 9,039,827 (75 pages, filed Aug. 7, 2015 by Petitioners Johns Manville Corporation and Johns Manville, Inc. in connection with $3^{rd}$ Petition for Inter Partes Review of U.S. Pat. No. 9,039,827).
Declaration of Dr. Elam Leed (11 pages, filed Jul. 29, Aug. 5, and Aug. 7, 2015 by Petitioners Johns Manville Corporation and Johns Manville, Inc. in connection with 1st, 2nd and 3rd Petition for Inter Partes Review of U.S. Pat. No. 9,039,827, respectively).
Declaration of Dr. Jonathan Vickers (10 pages, filed Jul. 29, Aug. 5, and Aug. 7, 2015 by Petitioners Johns Manville Corporation and Johns Manville, Inc. in connection with 1st, 2nd and 3rd Petition for Inter Partes Review of U.S. Pat. No. 9,039,827, respectively).
Petition for Inter Partes Review of U.S. Pat. No. 9,469,747 (67 pages, filed Mar. 20, 2018 by Petitioners Johns Manville Corporation and Johns Manville, Inc.).
Petition for Inter Partes Review of U.S. Pat. No. 9,828,287 (86 pages, filed Mar. 23, 2018 by Petitioners Johns Manville Corporation and Johns Manville, Inc.).
Petition for Inter Partes Review of U.S. Pat. No. 9,464,207 (78 pages, filed Mar. 28, 2018 by Petitioners Johns Manville Corporation and Johns Manville, Inc.).
Petition for Inter Partes Review of U.S. Pat. No. 9,926,464 (74 pages, filed Mar. 30, 2018 by Petitioners Johns Manville Corporation and Johns Manville, Inc.).

Office Action Granting Ex Parte Reexamination of U.S. Pat. No. 7,888,445, dated Dec. 24, 2013, in U.S. Appl. No. 90/013,029, 11 pages.
Office Action Granting Ex Parte Reexamination of U.S. Pat. No. 7,772,347, dated Dec. 24, 2013, in U.S. Appl. No. 90/013,030, 14 pages.
Office Action Granting Ex Parte Reexamination of U.S. Pat. No. 7,854,980, dated Apr. 15, 2014, in U.S. Appl. No. 90/013,156, 20 pages.
Declaration of Jan Rud Andersen submitted in Ex parte Reexamination U.S. Appl. No. 90/013,030, as Document OTH-C, Oct. 10, 2013, 4 pages.
Final Rejection in Ex Parte Reexamination of U.S. Pat. No. 7,888,445 (20 pages)—dated Jul. 24, 2015.
Final Rejection in Ex Parte Reexamination of U.S. Pat. No. 7,772,347 (23 pages)—dated Jul. 24, 2015.
Final Rejection in Ex Parte Reexamination of U.S. Pat. No. 7,854,980 (31 pages)—dated Aug. 18, 2015.
Advisory Action in Ex Parte Reexamination of U.S. Pat. No. 7,888,445 (4 pages)—dated Oct. 6, 2015.
Advisory Action in Ex Parte Reexamination of U.S. Pat. No. 7,772,347 (4 pages)—dated Oct. 6, 2015.
Advisory Action in Ex Parte Reexamination of U.S. Pat. No. 7,854,980 (4 pages)—dated Nov. 18, 2015.
Examiner's Answer in Ex Parte Reexamination of U.S. Pat. No. 7,888,445 (8 pages)—Mar. 23, 2016.
Examiner's Answer in Ex Parte Reexamination of U.S. Pat. No. 7,772,347 (8 pages)—Mar. 23, 2016.
Examiner's Answer in Ex Parte Reexamination of U.S. Pat. No. 7,854,980 (8 pages)—Mar. 22, 2016.
Decision of PTAB in Ex Parte Reexamination of U.S. Pat. No. 7,888,445 (17 pages)—Sep. 29, 2016.
Decision of PTAB in Ex Parte Reexamination of U.S. Pat. No. 7,772,347 (18 pages)—Sep. 29, 2016.
Decision of PTAB in Ex Parte Reexamination of U.S. Pat. No. 7,854,980 (22 pages)—Sep. 30, 2016.
Court of Appeals for Federal Circuit Judgment from Consolidated Appeal of PTAB Decisions in Ex Parte Reexamination of U.S. Pat. Nos. 7,888,445, 7,772,347 and 7,854,980 (5 pages)—Mar. 9, 2018.
Notice of Intent to Issue Ex Parte Reexamination Certificate for U.S. Pat. No. 7,772,347 (4 pages) dated Oct. 24, 2018.
Notice of Intent to Issue Ex Parte Reexamination Certificate for U.S. Pat. No. 7,888,445 (4 pages)—dated Dec. 7, 2018.
Decision of USPTO to Reopen Prosecution in Ex Parte Reexamination of U.S. Pat. No. 7,854,980 (7 pages)—Jan. 7, 2019.
Non-final Office Action from Reopened Prosecution in Ex Parte Reexamination of U.S. Pat. No. 7,854,980 (26 pages)—dated Apr. 3, 2019.
Final Office Action from Reopened Prosecution in Ex Parte Reexamination of U.S. Pat. No. 7,854,980 (11 pages)—dated Aug. 8, 2019.
Notice of Intent to Issue Ex Parte Reexamination Certificate for U.S. Pat. No. 7,854,980 (3 pages)—dated Oct. 29, 2019.
Notice of Intent to Issue Inter Partes Reexamination Certificate for U.S. Pat. No. 7,807,771 (4 pages)—dated Jan. 30, 2014.
Notice of Intent to Issue Inter Partes Reexamination Certificate for U.S. Pat. No. 7,854,980 (6 pages)—dated Aug. 31, 2017.
Decision of PTAB in Inter Partes Reexamination of U.S. Pat. No. 7,888,445 (34 pages)—May 1, 2015.
Decision of PTAB in Inter Partes Reexamination of U.S. Pat. No. 7,772,347 (36 pages)—May 1, 2015.
Decision of PTAB in Inter Partes Reexamination of U.S. Pat. No. 7,854,980 (25 pages)—Jul. 30, 2015.
Remand Order of PTAB in Inter Partes Reexamination of U.S. Pat. No. 7,888,445 (5 pages)—Dec. 9, 2015.
Remand Order of PTAB in Inter Partes Reexamination of U.S. Pat. No. 7,772,347 (5 pages)—Dec. 9 , 2015.
Examiner's Determination on Patent Owner Response/Requester Comments after Board Decision in Inter Partes Reexamination of U.S. Pat. No. 7,888,445 (22 pages)—Oct. 17, 2016.
Examiner's Determination on Patent Owner Response/Requester Comments after Board Decision in Inter Partes Reexamination of U.S. Pat. No. 7,772,347 (17 pages)—Oct. 17, 2016.

(56) References Cited

OTHER PUBLICATIONS

Court of Appeals for Federal Circuit Opinion/Judgment from Appeal of PTAB Decision in Inter Partes Reexamination of U.S. Pat. No. 7,854,980 (13 pages)—Feb. 27, 2017.
Final Decision of PTAB in Inter Partes Reexamination of U.S. Pat. No. 7,888,445 (25 pages)—dated Sep. 8, 2017.
Final Decision of PTAB in Inter Partes Reexamination of U.S. Pat. No. 7,772,347 (24 pages)—dated Sep. 8, 2017.
Decision of PTAB re Request for Rehearing in Inter Partes Reexamination of U.S. Pat. No. 7,888,445 (7 pages)—Feb. 12, 2018.
Decision of PTAB re Request for Rehearing in Inter Partes Reexamination of U.S. Pat. No. 7,772,347 (7 pages)—Feb. 12, 2018.
Court of Appeals for Federal Circuit Decision re Consolidated Appeal of PTAB Decision in Inter Partes Reexamination of U.S. Pat. No. 7,772,347 and U.S. Pat. No. 7,888,445 (14 pages)—Oct. 15, 2019.
Remand Order of PTAB in Inter Partes Reexamination of U.S. Pat. No. 7,888,445 (3 pages)—Jul. 1, 2020.
Remand Order of PTAB in Inter Partes Reexamination of U.S. Pat. No. 7,772,347 (3 pages)—Jul. 1, 2020.
U.S. Pat. No. 2,965,504—Part 1 (10 pages).
U.S. Pat. No. 2,965,504—Part 2 (14 pages).
U.S. Pat. No. 2,965,504 — Part 3 (14 pages).
Gogek Attorney Comments re U.S. Pat. No. 2,965,504—Apr. 6, 1960 (3 pages).
Gogek Affidavit Under Rule 132 re U.S. Pat. No. 2,965,504—Feb. 26, 1960 (3 pages).
Decision of PTAB regarding Institution of Inter Partes Review for U.S. Pat. No. 8,114,210 (20 pages)—Oct. 21, 2015.
Final Written Decision of PTAB regarding Inter Partes Review of U.S. Pat. No. 8,114,210 (39 pages)—dated Oct. 19, 2016.
Court of Appeals for Federal Circuit Judgment from Appeal of PTAB Decision in Inter Partes Review of U.S. Pat. No. 8,114,210 (5 pages)—Jan. 16, 2018.
Decision of USPTO Granting Ex Parte Re-exam of U.S. Pat. No. 8,114,210 (11 pages)—Apr. 9, 2020.
Decision1 of PTAB declining Institution of Inter Partes Review for U.S. Pat. No. 8,940,089 (16 pages)—Dec. 17, 2015.
Decision2 of PTAB declining Institution of Inter Partes Review for U.S. Pat. No. 8,940,089 (19 pages)—Dec. 17, 2015.
Decision3 of PTAB declining Institution of Inter Partes Review for U.S. Pat. No. 8,940,089 (14 pages)—Dec. 17, 2015.
Decision1 of PTAB declining Institution of Inter Partes Review for U.S. Pat. No. 9,039,827 (16 pages)—Jan. 4, 2016.
Decision2 of PTAB declining Institution of Inter Partes Review for U.S. Pat. No. 9,039,827 (19 pages)—Jan. 4, 2016.
Decision3 of PTAB declining Institution of Inter Partes Review for U.S. Pat. No. 9,039,827 (14 pages)—Jan. 4, 2016.
Decision of PTAB denying Institution of Inter Partes Review for U.S. Pat. No. 9,926,464 (29 pages)—Oct. 2, 2018.
Decision of PTAB denying Institution of Inter Partes Review for U.S. Pat. No. 9,464,207 (28 pages)—Oct. 2, 2018.
Decision of PTAB denying Institution of Inter Partes Review for U.S. Pat. No. 9,469,747 (29 pages)—Oct. 3, 2018.
Decision of PTAB denying Institution of Inter Partes Review for U.S. Pat. No. 9,828,287 (22 pages)—Oct. 16, 2018.
Decision of USPTO Granting Ex Parte Re-exam of U.S. Pat. No. 9,828,287 (13 pages)—Jul. 17, 2020.
Decision of USPTO Granting Ex Parte Re-exam of U.S. Pat. No. 9,464,207 (14 pages)—Jul. 31, 2020.
Decision of USPTO Granting Ex Parte Re-exam of U.S. Pat. No. 9,926,464 (18 pages)—Aug. 5, 2020.
Statement of Revocation Grounds re GB2496951—Claimant Rockwool International (May 21, 2018, 22 pages).
Statement of Revocation Grounds re GB2451719—Claimant Rockwool International (May 18, 2018, 22 pages).
Expert Report re Revocation of GB2451719 and GB2496951—Claimant Rockwool International (Nov. 12, 2018, 11 pages).
*United Kingdom Intellectual Property Office, Decision in Rockwool International v. Knauf Insulation Limited*, Application under Section 72 for revocation of patents GB2451719 and GB2496951 (May 28, 2019—18 pages).
Decision of EPO Board of Appeal re Added Matter vis-à-vis EP06788492.4 (Jul. 17, 2019—14 pages).
Decision of USPTO Granting Ex Parte Re-exam of U.S. Pat. No. 8,940,089 (17 pages)—dated Oct. 16, 2020.
Decision of USPTO Granting Ex Parte Re-exam of U.S. Pat. No. 9,039,827 (16 pages)—dated Oct. 16, 2020.
Decision of USPTO Granting Ex Parte Re-exam of U.S. Pat. No. 9,469,747 (16 pages)—dated Nov. 9, 2020.

* cited by examiner

CARBOHYDRATE BINDERS AND MATERIALS MADE THEREWITH

CROSS-REFERENCE TO RELATED APPLICATIONS

This application is a continuation of U.S. patent application Ser. No. 16/241,049, filed Jan. 7, 2019, which is a continuation of U.S. patent application Ser. No. 15/276,283 (now abandoned), filed Sep. 26, 2016, which is a continuation of U.S. patent application Ser. No. 13/696,452 (now U.S. Pat. No. 9,493,603), filed Nov. 6, 2012, which is a national stage entry under 35 U.S.C. § 371(b) of International Application No. PCT/EP2011/057364, filed May 7, 2011, which claims the benefit under 35 U.S.C. § 119(e) of U.S. Provisional Application Ser. No. 61/332,452, filed May 7, 2010, the disclosures of which are incorporated herein by reference in their entirety.

TECHNICAL FIELD

This disclosure relates to a binder formulation and materials made therewith comprising a carbohydrate-based binder and a method for preparing the same. In particular, a binder comprising the reaction products of a carbohydrate and a nucleophile and materials made therewith is described.

BACKGROUND

Binders are useful in fabricating articles because they are capable of consolidating non- or loosely-assembled matter. For example, binders enable two or more surfaces to become united. In particular, binders may be used to produce products comprising consolidated fibers. Thermosetting binders may be characterized by being transformed into insoluble and infusible materials by means of either heat or catalytic action. Examples of a thermosetting binder include a variety of phenol-aldehyde, urea-aldehyde, melamine-aldehyde, and other condensation-polymerization materials like furane and polyurethane resins. Binder compositions containing phenol-aldehyde, resorcinol-aldehyde, phenol/aldehyde/urea, phenol/melamine/aldehyde, and the like are used for the bonding of fibers, textiles, plastics, rubbers, and many other materials.

The mineral wool and fiber board industries have historically used a phenol formaldehyde binder to bind fibers. Phenol formaldehyde type binders provide suitable properties to the final products; however, environmental considerations have motivated the development of alternative binders. One such alternative binder is a carbohydrate based binder derived from reacting a carbohydrate and a multiprotic acid, for example, U.S. Published Application No. 2007/0027283 and Published PCT Application WO2009/019235. Another alternative binder is the esterification products of reacting a polycarboxylic acid and a polyol, for example, U.S. Published Application No. 2005/0202224. Because these binders do not utilize formaldehyde as a reagent, they have been collectively referred to as formaldehyde-free binders.

One area of current development is to find a replacement for the phenol formaldehyde type binders across the entire range of products in the building and automotive sector (e.g. fiberglass insulation, particle boards, office panels, and acoustical sound insulation). In particular, the previously developed formaldehyde-free binders may not possess all of the desired properties for all the products in this sector. For example, acrylic acid and poly(vinylalcohol) based binders have shown promising performance characteristics. However, these are relatively more expensive than phenol formaldehyde binders, are derived essentially from petroleum-based resources, and have a tendency to exhibit lower reaction rates compared to the phenol formaldehyde based binder compositions (requiring either prolonged cure times or increased cure temperatures). Carbohydrate-based binder compositions are made of relatively inexpensive precursors and are derived mainly from renewable resources; however, these binders may also require reaction conditions for curing that are substantially different from those conditions under which the traditional phenol formaldehyde binder system cured. As such, facile replacement of phenol formaldehyde type binders with an existing alternative has not been readily achievable.

SUMMARY

According to the present disclosure, a carbohydrate based binder is described. The binder composition has properties that make it useful for a variety of applications; particularly, the binder may be used to bind loosely assembled matter such as fibers.

In illustrative embodiments, the present disclosure relates to a binder comprising a polymeric product of a carbohydrate reactant and a nucleophile. In one embodiment, the carbohydrate reactant is a polysaccharide. In one embodiment, the carbohydrate reactant is a monosaccharide or a disaccharide. In another embodiment, the carbohydrate is a monosaccharide in its aldose or ketose form. In another embodiment, the carbohydrate reactant is selected from the group consisting of dextrose, xylose, fructose, dihydroxyacetone, and mixtures thereof. In another embodiment, the polymeric product is a thermoset polymeric product.

In illustrative embodiments, the nucleophile is a di-functional. In another embodiment, the nucleophile is $R_1$-Q-$R_2$, wherein Q is alkyl, cycloalkyl, heteroalkyl, or cycloheteroalkyl, each of which is optionally substituted having a nucleophilic moiety and a stabilization moiety, $R_1$ is selected from the group consisting of an amine, an azide, a cyanate, an isocyanate, a thiol, a disulfide, a thiocyanate, a halogen, a haloformyl, a carboxyl, a carboxylate, a hydroxyl, and an alkoxide, and $R_2$ is selected from the group consisting of an amine, an amide, an imine, an imide, a nitro, a nitrate, a pyridine, a phosphate, a phosphono, a hydroxyl, a hydrogen, a sulphono, a sulpho, a sulfinyl, and a sulfhydryl (thiol). In one embodiment, the nucleophile includes an amine functional group.

In illustrative embodiments, the mole ratio of the carbohydrate reactant to the nucleophile is in the range of about 1:1 to about 30:1. In another embodiment, the mole ratio of the carbohydrate reactant to the nucleophile is in the range of about 2:1 to about 10:1. In another embodiment, an aqueous extract of the polymeric product has a pH in the range of about 5 to about 9. In another embodiment, an aqueous extract of the polymeric product is essentially colorless. In yet another embodiment, the polymeric product is phenol-free and/or formaldehyde-free. In another embodiment, an aqueous extract of the polymeric product is capable of reducing Benedict's reagent. In another embodiment, the polymeric product absorbs light between 400 and 500 nm, for example, in one embodiment, at 420 nm.

In an illustrative embodiment, a method of making a collection of matter bound with a polymeric binder comprises preparing a solution containing reactants for producing the polymeric binder and a solvent, wherein the reactants include a carbohydrate reactant and a nucleophile; disposing the solution onto the collection of matter; volatilizing the solvent to form an uncured product, and subjecting the uncured product to conditions that cause the carbohydrate reactant and the nucleophile to polymerize to form the polymeric binder. In one embodiment, the collection of matter comprises fibers selected from the group consisting of mineral fibers (slag wool fibers, rock wool fibers, or glass fibers), aramid fibers, ceramic fibers, metal fibers, carbon fibers, polyimide fibers, polyester fibers, rayon fibers, and cellulosic fibers. In another embodiment, the collection of matter comprises particulates such as coal or sand. In another embodiment, the collection of matter is glass fibers. In yet another embodiment, the glass fibers are present in the range from about 70% to about 99% by weight. In another embodiment, the collection of matter comprises cellulosic fibers. For example, the cellulosic fibers may be wood shavings, sawdust, wood pulp, or ground wood. In yet another embodiment, the cellulosic fibers may be other natural fibers such as jute, flax, hemp, or straw.

In illustrative embodiments, the method of making a collection of matter bound with a polymeric binder further includes preparing a solution by adding an amount of a carbohydrate reactant and an amount of a nucleophile so that the molar ratio is in the range of about 2:1 to about 10:1, respectively. In one embodiment, preparing the solution includes adding the carbohydrate reactant and the nucleophile to an aqueous solution. In another embodiment, preparing the solution includes adjusting the pH of the solution to within the range of about 8 to about 13, for example, in one embodiment, the range of about 8 to about 12.

In illustrative embodiments, the present disclosure relates to a composition comprising a collection of matter and a binder; the binder comprising the polymeric products of a reaction between a carbohydrate reactant and a nucleophile, the polymeric products being substantially water insoluble. In one embodiment, the collection of matter includes mineral fibers (slag wool fibers, rock wool fibers, or glass fibers), aramid fibers, ceramic fibers, metal fibers, carbon fibers, polyimide fibers, polyester fibers, rayon fibers, and cellulosic fibers. For example, cellulosic fibers include wood shavings, sawdust, wood pulp, and/or ground wood. In one embodiment, the carbohydrate reactant is selected from the group consisting of dextrose, xylose, fructose, dihydroxyacetone, and mixtures thereof. In another embodiment, the nucleophile is selected from the group consisting of a diamine, triamine, tetramine, and pentamine. In one embodiment, the nucleophile is $R_1$-Q-$R_2$, wherein Q is alkyl, cycloalkyl, heteroalkyl, or cycloheteroalkyl, each of which is optionally substituted, $R_1$ is a nucleophilic moiety, and $R_2$ is a stabilization moiety. In one embodiment, $R_1$ is selected from the group consisting of an amine, an azide, a cyanate, an isocyanate, a thiol, a disulfide, a thiocyanate, a halogen, a haloformyl, a carboxyl, a carboxylate, a hydroxyl, and an alkoxide. In another embodiment, $R_2$ is selected from the group consisting of an amine, an amide, an imine, an imide, a nitro, a nitrate, a pyridine, a phosphate, a phosphono, a hydroxyl, a hydrogen, a sulphono, a sulpho, a sulfinyl, and a sulfhydryl (thiol).

In another embodiment, the composition further comprises a silicon-containing compound. In one embodiment the silicon-containing compound is a functionalized silylether or a functionalized alkylsilylether, such as for example, an amino-functionalized alkylsilylether. For example, in one embodiment, the silicon-containing compound may be gamma-aminopropyltriethoxysilane, gamma-glycidoxypropyltrimethoxysilane, or aminoethylaminopropyltrimethoxysilane, or a mixture thereof. In another embodiment, the silicon-containing compound may be an aminofunctional oligomeric siloxane. In another embodiment, the composition comprises a corrosion inhibitor selected from the group consisting of dedusting oil, monoammonium phosphate, sodium metasilicate pentahydrate, melamine, tin(II) oxalate, and a methylhydrogen silicone fluid emulsion.

DETAILED DESCRIPTION

Figure 1:
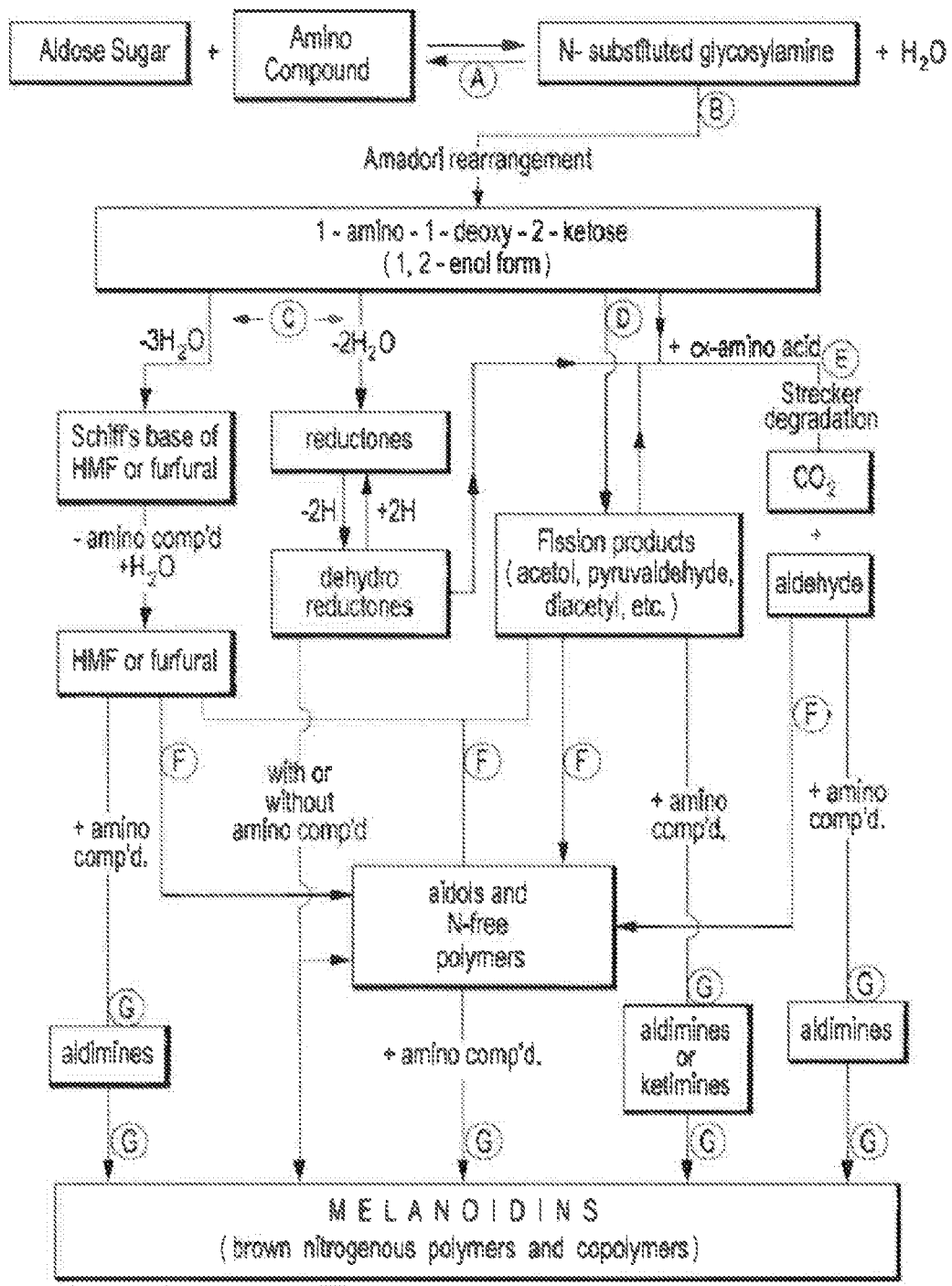
FIG. 1 shows a schematic of a Maillard reaction, which culminates in the production of melanoidins.

While the invention is susceptible to various modifications and alternative forms, specific embodiments will herein be described in detail. It should be understood, however, that there is no intent to limit the invention to the particular forms described, but on the contrary, the intention is to cover all modifications, equivalents, and alternatives falling within the spirit and scope of the invention.

The present disclosure relates to a binder composition having unexpected utility in consolidating non- or loosely-assembled matter. The binder composition represents an unexpected advancement in the current state of technology in the area of binder compositions. Specifically, the binder offers improvements in performance and provides for more simplified and advantageous manufacturing methodologies, while maintaining the environmentally sound advantages that are characteristic of a carbohydrate based binder system.

As used herein, the term binder solution is the solution of chemicals which can be substantially dehydrated to form an uncured binder. As used herein, the binder or binder composition may be cured, uncured, or partially cured. The composition of the uncured binder is referred to as an uncured binder composition. An uncured binder is a substantially dehydrated mixture of chemicals which can be cured to form a cured binder. Substantially dehydrated means that the solvent (typically water or a mixture thereof) used to make the binder solution is vaporized to the extent that the viscosity of the remaining material (comprising the binder reactants and solvent) is sufficiently high to create cohesion between the loosely assembled matter; thus, the remaining material is an uncured binder. In one embodiment, the solvent is less than 65% of the total weight of the remaining material. In another embodiment, a substantially dehydrated binder has a moisture content between about 5% and about 65% water by weight of total binder. In another embodiment, the solvent may be less than 50% of the total weight of the remaining material. In yet another embodiment, the solvent may be less than 35% of the total weight of the remaining material. In another embodiment, a substantially dehydrated binder has between about 10% and about 35% water by weight of total binder. In another embodiment, the solvent may comprise less than about 20% of the total weight of the remaining material.

In illustrative embodiments, an uncured binder may be colorless, white, off white, ochre or yellow to brownish sticky substance that is, at least partially, water soluble. As used herein, the term cured binder describes the polymeric product of curing the uncured binder composition. The cured binder may have a characteristic brown to black color. While described as brown or black, another characteristic is that the binder tends to absorb light over a broad range of wavelengths. In particular, there may be higher absorbance at approximately 420 nm. As the polymer is extensively cross-linked, the cured binder is substantially insoluble. For example, the binder is predominantly insoluble in water. As described herein, the uncured binder provides sufficient binding capacity to consolidate fibers; however, the cured binder imparts the robust, long-lasting durability and physical properties commonly associated with cross-linked polymers.

In illustrative embodiments, the binder reactants described herein are soluble in water and the binder solution is a solution of the binder reactants in an aqueous solution. In one embodiment, a surfactant is included in the aqueous solution to increase the solubility or dispersability of one or more binder reactants or additives. For example, a surfactant may be added to the aqueous binder solution to enhance the dispersibility of a particulate additive. In one embodiment, a surfactant is used to create an emulsion with a non-polar additive or binder reactant. In another embodiment, the binder solution comprises about 0.01% to about 5% surfactant by weight based on the weight of the binder solution.

In illustrative embodiments, the binder solutions described herein can be applied to mineral fibers (e.g., sprayed onto the mat or sprayed onto the fibers as they enter the forming region), during production of mineral fiber insulation products. Once the binder solution is in contact with the mineral fibers the residual heat from the mineral fibers (note that the glass fibers, for example, are made from molten glass and thus contain residual heat) and the flow of air through and/or around the product will cause a portion of the water to evaporate from the binder solution. Removing the water leaves the remaining components of the binder on the fibers as a coating of viscous or semi-viscous high-solids mixture. This coating of viscous or semi-viscous high-solids mixture functions as a binder. At this point, the mat has not been cured. In other words, the uncured binder functions to bind the fibers in the mat.

Furthermore, it should be understood that the above described uncured binders can be cured. For example, the process of manufacturing a cured insulation product may include a subsequent step in which heat is applied as to cause a chemical reaction in the uncured binder composition. For example, in the case of making fiberglass insulation products, after the binder solution has been applied to the fibers and dehydrated, the uncured insulation product may be transferred to a curing oven. In the curing oven the uncured insulation product is heated (e.g., from about 300° F. to about 600° F. [from about 150° C. to about 320° C.]), causing the binder to cure. The cured binder is a formaldehyde-free, water-resistant binder that binds the glass fibers of the insulation product together. Note that the drying and thermal curing may occur either sequentially, simultaneously, contemporaneously, or concurrently.

In illustrative embodiments, an uncured fiber product comprises about 3% to about 40% of dry binder solids (total uncured solids by weight). In one embodiment, the uncured fiber product comprises about 5% to about 25% of dry binder solids. In another embodiment, the uncured fiber product comprises about 50% to about 97% fibers by weight.

As mentioned herein with respect to a binder on mineral fibers, a cured binder is the product of curing binder reactants. The term cured indicates that the binder has been exposed to conditions so as to initiate a chemical change. Examples of these chemical changes include, but are not limited to, (i) covalent bonding, (ii) hydrogen bonding of binder components, and (iii) chemically cross-linking the polymers and/or oligomers in the binder. These changes may increase the binder's durability and solvent resistance as compared to the uncured binder. Curing a binder may result in the formation of a thermoset material. In addition, a cured binder may result in an increase in adhesion between the matter in a collection as compared to an uncured binder. Curing can be initiated by, for example, heat, microwave radiation, and/or conditions that initiate one or more of the chemical changes mentioned above. While not limited to a particular theory, curing may include the reaction of the carbohydrate and the nucleophile in a nucleophilic addition reaction or nucleophilic addition-elimination reaction.

In a situation where the chemical change in the binder results in the release of water, e.g., polymerization and cross-linking, a cure can be determined by the amount of water released above that which would occur from drying alone. The techniques used to measure the amount of water released during drying as compared to when a binder is cured, are well known in the art.

In illustrative embodiment, the nucleophile is a nitrogen containing compound. In one embodiment, the cured binder composition comprises a nitrogenous polymer. In one embodiment, the nitrogenous polymer is brown to black in color. While not limited to a particular theory, the cured binder composition comprises a mixture of high molecular weight polymers. The high molecular weight polymers may be characterized as being highly cross-linked. Furthermore, the high molecular weight polymers may be characterized as being brown, complex, furan ring-containing and nitrogen-containing polymers. High molecular weight, as used herein, includes those polymers having a molecular weight in excess of 100,000 Daltons. Being comprised of highly cross-linked polymeric chains, the molecular weight of the high molecular weight polymers described herein approaches infinity. Accordingly, the molecular weight of the high molecular weight polymers may be a function of the mass and physical dimensions of the polymer being analyzed. For example, a unitary sample of melanoidins having a mass of 3 grams may be presumed to comprise a single polymeric molecule due to the extensive cross-linking. Accordingly, the molecular weight of the polymer would be approximately $1.8 \times 10^{24}$ grams per mole (being the product of the sample mass and Avogadro's number). As used herein, a high molecular weight polymer includes polymers with a molecular weight in the order of between about $1 \times 10^5$ and about $1 \times 10^{24}$ grams per mole.

While not be limited to a particular theory, it is understood that high molecular weight polymers vary in structure according to the reactants and conditions of preparation. It is also known that high molecular weight polymers possess a carbon to nitrogen ratio which increases with temperature and time of heating. Furthermore, high molecular weight polymers possess saturated, unsaturated and aromatic character. In one embodiment, the high molecular weight polymers possessed a degree of unsaturation and aromaticity that increased with temperature (cure temperature) and time of heating (cure time). The high molecular weight polymers also contained the C-1 of those sugars incorporated as reactants in a variety of structures within the polymer. The high molecular weight polymers may also contain carbonyl, carboxyl, amine, amide, pyrrole, indole, azomethine, ester, anhydride, ether, methyl and/or hydroxyl groups. Depending on the complexity of the structure, infrared spectroscopy may be useful in the identification of one or more of these functional groups. While not so classified here, one of ordinary skill would appreciate that the binder may be classifiable according to the existence of a particular bond present such as a polyester, polyether, polyamide, etc.

Another manner in which the binder is characterizable is through analysis of the gaseous compounds produced during pyrolysis of the cured binder. Gas pyrolysis of a cured binder within the scope of the present disclosure may yield approximately 0.5 to about 15% (by relative peak area) of one or more of the following compounds: 2-cyclopenten-1-one, 2,5-dimethyl-furan, furan, 3-methyl-2,5-furandione, phenol, 2,3-dimethyl-2-cyclopenten-1-one, 2-methyl phenol, 4-methyl phenol, 2,4-dimethyl-phenol, dimethylphthalate, octadecanoic acid, or erucylamide. Fingerprinting in pyrolysis gas chromatography mass spectrometry (Py GC-MS) carried out at 770° C. of a binder sample prepared using hexamethylenediamine as the polyamine component shows pyridine and a number of components which are pyrrole or pyridine derivatives (a methyl pyridine, a methyl pyrrole, dimethyl pyridines, a dimethyl pyrrole, an ethyl methyl pyrrole, and other pyrrole related N-containing components). Another manner in which the binder may be identified is whether a solution containing the binder (or an extract solution) is capable of reducing Benedict's reagent. In one embodiment, a solution in contact with the binder or an aqueous extract thereof reduces Benedict's reagent.

One aspect of the present disclosure is that the binders described herein are environmentally friendly. Parallel to advancing government regulation, the present disclosure describes a binder that may be made formaldehyde-free. Additionally, the chemistry described herein is essentially free of formaldehyde and phenol. In this sense, neither formaldehyde nor phenol is used as a reagent within the scope of the present disclosure. While both may be added to obtain a binder with potentially useful properties, one aspect of the present disclosure is a binder that can be made free from both of these reactants. In another aspect, the present binder composition may be manufactured without the use of volatile reactants. In one embodiment, the nucleophile and the carbohydrate are both non-volatile reactants. As used herein, a volatile reactant is one that has a vapor pressure greater than 10 kPa at 20° C. Similarly, as used herein, a non-volatile reactant has a vapor pressure of less than about 10 kPa at 20° C. Specifically and as an example, the present binder may be manufactured without the addition of ammonia or an ammonia releasing compound. In one embodiment, the nucleophile has a vapor pressure of less than about 0.5 kPa at 60° C.

Another environmentally friendly aspect of the present disclosure is that the primary reactants of the binder are carbohydrates. Carbohydrates are considered a renewable resource. However, the current state of the art primarily uses petroleum-derived reactants for the manufacture of binder compositions. In another aspect, the binder is made through chemical reactions which can occur at lower temperatures than those comparable systems described in the prior art. As such, the curing ovens and manufacturing equipment can be operated at lower temperatures, saving valuable resources. In the alternative and in a related manner, the binder described herein cures more quickly than comparable binders currently used when subjected to similar curing temperatures. Accordingly, through either approach, one aspect of the present disclosure is that the carbon footprint of a formed product using the presently disclosed binder may be substantially reduced compared to a comparable binder made according to the current state of the art, for example a phenol formaldehyde based product.

In addition to the environmental benefits, the present binder composition and materials made therewith can be made having performance characteristics equivalent or exceeding those of comparable binder systems, for example, phenol formaldehyde binders. In one aspect, a binder according to the present disclosure provides articles made therewith sufficient tensile strength to allow for die-cutting, fabrication, lamination, and installation in OEM applications. In one aspect, a binder according to the present disclosure has water hold-up (weatherability) comparable to that of a phenol formaldehyde binder. Other performance characteristic that may be relevant for a particular application include product emissions, density, loss on ignition, thickness recovery, dust, tensile strength, parting strength, durability of parting strength, bond strength, water absorption, hot surface performance, corrosivity on steel, flexural rigidity, stiffness-rigidity, compressive resistance, conditioned compressive resistance, compressive modulus, conditioned compressive modulus, and smoke development on ignition. One aspect of the present disclosure is that the extract of the cured binder is essentially pH neutral, for example between a pH of 6 and 8. Another aspect of the present disclosure is that the present binder enables the manufacture of products having comparable relevant performance characteristics to phenol formaldehyde binder compositions.

Illustratively, in one embodiment, a binder according to the present disclosure invention has the advantage of yielding essentially colorless aqueous extracts. This feature of the present disclosure makes the binder desirable in applications such as ceiling tiles, furniture, or office panels, wherein the finished product may come into contact with water. A cured manufactured good made with the present binder shows an excellent resistance to discoloration or bleeding after coming in contact with moisture or water. Furthermore, in such an embodiment, the water that contacts the binder does not leave a residual color on other articles or parts which it may contact subsequent to contact the binder. For example, in one embodiment, the binder may be used to bind glass fibers in an office panel application. Covering the bound fiberglass composition may be a light colored fabric. Advantageously, in one embodiment, water contacting the fiberglass composition does not leave a colored residue upon the fabric after the office panel has dried.

In addition to the performance characteristics, the manufacturing processes and methods involving the presently disclosed binder have a number of unexpected advantages over previously described binders. In one aspect, as previously described with respect to the environmental benefits, the present binder may be manufactured without the use of highly volatile reactants. Accordingly, manufacturing emission controls are under a reduced burden. Furthermore, the reaction efficiency is higher because reactant loss due to vaporization is reduced. Accordingly, one aspect of the present disclosure is that the compounds used herein are substantially non-volatile, thus the steps one must take to mitigate undesirable emissions are reduced.

According to another aspect, the reactants that react to form a binder are sufficiently slow to react such that a one step/one pot binder system can be used. According to this aspect, the reactant compounds are sufficiently slow to react that they can be added to a single reactant solution and stored for a reasonable amount of time during which they can be applied to a product using one distribution system. This contrasts with those binder systems which react at low temperatures resulting in insoluble reaction products within binder solution delivery systems. As used here, a reasonable amount of time for storage without substantial (>5%) polymeric precipitation is two weeks.

Another aspect of the present disclosure is that, although the binder is sufficiently unreactive at room temperature conditions to facilitate a one-pot approach, it is sufficiently reactive at elevated temperatures to cure at very low temperatures and/or very short curing residency times. In one respect, the lowered curing temperature reduces the risk of an insulation product undergoing flameless combustion and/or causing line fires. As used here, very low temperatures are characterized as less than or equal to about 120° C. As used here, very short cure times are less than or equal to about 4 min.

In illustrative embodiments, the binder composition includes an acid or an acid salt to increase the shelf life of the uncured binder or binder solution. While this acid is not a reactant or a catalyst, it may be included to slow or inhibit the binder reactants from forming the binder while the binder solution or uncured binder is being maintained under storage conditions. For example, a volatile acid or acid salt may be included in the binder solution or uncured binder that slows or inhibits the curing reaction at ambient conditions. However, the acid may be removed by heating the binder solution or uncured binder so that the acid is volatilized and the pH of the binder solution or uncured binder increases. In one embodiment, the binder composition includes a shelf-life extending acid. In another embodiment, the binder composition includes a mole ratio of shelf-life extending acid to nucleophile of about 1:20 to about 1:1.

Another aspect of the present disclosure is a binder having a cure rate, cycle time, and cure temperature which meets or exceeds those cure rates that a comparable phenol and formaldehyde type binder may exhibit within the scope of a comparable use. In this respect, the present binder can be used as a direct replacement to phenol formaldehyde resins in applications without modification to the equipment. Furthermore, the present binder enables the modification of the curing temperature and times so that both the reaction temperatures and cure times may be reduced. This reduction has the effect of reducing the energy consumption of the process overall and reduces the environmental impact of manufacturing the product. Furthermore, the lower cure temperatures have the further effect of increasing the safety of manufacturing process. Another effect of the lower cure temperatures is a reduction in the risk of flameless combustion or fire.

In the manufacture of insulation products, the heat released by the exothermic curing reaction may result in self-heating of the product. Self-heating is typically not problematic so long as the heat dissipates from the product. However, if the heat increases the temperature of the product to the point where oxidative processes commence, the self-heating may cause significant damage to the product. For example, flameless combustion or oxidation may occur when the temperature of the insulation product exceeds about 425° F. (210° C.). At these temperatures, the exothermic combustion or oxidation processes promote further self-heating and the binder may be destroyed. Furthermore, the temperature may increase to a level in which fusing or devitrification of the glass fibers is possible. Not only does this damage the structure and value of the insulation product, it may also create a fire hazard.

Another aspect of the present disclosure is that the binder system is essentially non-corrosive with or without the addition of corrosion inhibitors. Furthermore, the binder system does not require the addition of any organic or inorganic acid or salts thereof as catalyst or active ingredient. Accordingly, one aspect of the present binder is that it may be made essentially acid-free. Furthermore, the binder may be manufactured under entirely alkaline conditions. As used here, the term acid includes those compounds which are characterizable primarily for their acidic character such multiprotic inorganic and organic acids (e.g. sulfuric acid and citric acid). This aspect reduces the wear and maintenance requirements of the manufacturing equipment and enhances worker safety.

In illustrative embodiments, a binder comprises a polymeric product of a carbohydrate reactant and a nucleophile. As used herein, the term carbohydrate reactant refers to a monosaccharide, a disaccharide, a polysaccharide, or a reaction product thereof. In one embodiment, the carbohydrate reactant may be a reducing sugar. As used herein, reducing sugar indicates one or more sugars that contain aldehyde groups, or that can isomerize, i.e., tautomerize, to contain aldehyde groups, which groups may be oxidized with, for example, $Cu^{+2}$ to afford carboxylic acids. It is also appreciated that any such carbohydrate reactant may be optionally substituted, such as with hydroxy, halo, alkyl, alkoxy, and the like. It is further appreciated that in any such carbohydrate reactant, one or more chiral centers are present, and that both possible optical isomers at each chiral center are contemplated to be included in the invention described herein. Further, it is also to be understood that various mixtures, including racemic mixtures, or other diastereomeric mixtures of the various optical isomers of any such carbohydrate reactant, as well as various geometric isomers thereof, may be used in one or more embodiments described herein. While non-reducing sugars, for instance sucrose, may not be preferable, they may none-the-less be useful within the scope of the present disclosure by in-situ conversion to a reducing sugar (i.e. conversion of sucrose to invert sugar is a method known in the art). Further, it is also understood that a monosaccharide, a disaccharide, or polysaccharide may be partially reacted with a precursor to form a carbohydrate reaction product. To the extent that the carbohydrate reaction product is derived from a monosaccharide, a disaccharide, or a polysaccharide and maintains similar reactivity with the nucleophile to form reaction products similar to those of a monosaccharide, a disaccharide, or a polysaccharide with a nucleophile, the carbohydrate reaction product is within the scope of term carbohydrate reactant.

In one aspect, any carbohydrate reactant should be sufficiently nonvolatile to maximize its ability to remain available for reaction with the nucleophile. The carbohydrate reactant may be a monosaccharide in its aldose or ketose form, including a triose, a tetrose, a pentose, a hexose, or a heptose; or a polysaccharide; or combinations thereof. For example, when a triose serves as the carbohydrate reactant, or is used in combination with other reducing sugars and/or a polysaccharide, an aldotriose sugar or a ketotriose sugar may be utilized, such as glyceraldehyde and dihydroxyacetone, respectively. When a tetrose serves as the carbohydrate reactant, or is used in combination with other reducing sugars and/or a polysaccharide, aldotetrose sugars, such as erythrose and threose; and ketotetrose sugars, such as erythrulose, may be utilized. When a pentose serves as the carbohydrate reactant, or is used in combination with other reducing sugars and/or a polysaccharide, aldopentose sugars, such as ribose, arabinose, xylose, and lyxose; and ketopentose sugars, such as ribulose, arabulose, xylulose, and lyxulose, may be utilized. When a hexose serves as the carbohydrate reactant, or is used in combination with other reducing sugars and/or a polysaccharide, aldohexose sugars, such as glucose (i.e., dextrose), mannose, galactose, allose, altrose, talose, gulose, and idose; and ketohexose sugars, such as fructose, psicose, sorbose and tagatose, may be utilized. When a heptose serves as the carbohydrate reactant, or is used in combination with other reducing sugars and/or a polysaccharide, a ketoheptose sugar such as sedoheptulose may be utilized. Other stereoisomers of such carbohydrate reactants not known to occur naturally are also contemplated to be useful in preparing the binder compositions as described herein. In one embodiment, the carbohydrate reactant is high fructose corn syrup.

In illustrative embodiments, the carbohydrate reactant is a polysaccharide. In one embodiment, the carbohydrate reactant is a polysaccharide with a low degree of polymerization. In one embodiment, the polysaccharide is molasses, starch, cellulose hydrolysates, or mixtures thereof. In one embodiment, the carbohydrate reactant is a starch hydrolysate, a maltodextrin, or a mixture thereof. While carbohydrates of higher degrees of polymerization may not be preferable, they may none-the-less be useful within the scope of the present disclosure by in-situ depolymerization (i.e. depolymerization through ammoniation at elevated temperatures is a method known in the art).

Furthermore, the carbohydrate reactant may be used in combination with a non-carbohydrate polyhydroxy reactant. Examples of non-carbohydrate polyhydroxy reactants which can be used in combination with the carbohydrate reactant include, but are not limited to, trimethylolpropane, glycerol, pentaerythritol, polyvinyl alcohol, partially hydrolyzed polyvinyl acetate, fully hydrolyzed polyvinyl acetate, and mixtures thereof. In one aspect, the non-carbohydrate polyhydroxy reactant is sufficiently nonvolatile to maximize its ability to remain available for reaction with a monomeric or polymeric polyamine. It is appreciated that the hydrophobicity of the non-carbohydrate polyhydroxy reactant may be a factor in determining the physical properties of a binder prepared as described herein.

As used herein, a nucleophile is a reagent that forms a bond to its reaction partner (the electrophile) by donating both bonding electrons. As used herein, an electrophile is a reagent that forms a bond to its reaction partner (the nucleophile) by accepting both bonding electrons from that reaction partner. Illustratively, the electrophile is the carbohydrate described herein. Specifically, the electrophilic group is the carbon associated with the aldose or ketose form of the carbohydrate. For example, C-1 of glucose is electropositive due to the aldose functionality and reacts with a nucleophile of the present disclosure. In another example, C-2 of fructose is electropositive due to the ketose functionality and reacts with a nucleophile of the present disclosure. While described as an electrophile in its initial interaction with the nucleophile, one skilled in the art will appreciate that the carbohydrate is not limited to acting only as an electrophile within the scope of reactions which may occur. For example, the hydroxyl groups of the carbohydrate may act as a nucleophile depending on the presence of a reactive nucleophile. Furthermore, while the initial reaction between the nucleophile and the carbohydrate may correctly classify the carbohydrate as an electrophile, the product of that reaction may exhibit both nucleophilic and electrophilic functionality in further reactions.

In illustrative embodiments, the nucleophile is sufficiently nucleophilic to react with a carbohydrate in its aldose or ketose form in a solution having a pH as described herein and at a temperature described herein. In one embodiment, the nucleophile includes a cationic stabilization moiety. As used herein, a cationic stabilization moiety is a chemical group on the nucleophile which stabilizes the cation that forms upon the nucleophilic attack. For example, one nucleophile within the scope of the present disclosure is a diamine. Upon nucleophilic attack of a carbonyl by a primary amine, a cation of a Schiff base is formed. While the diamine's first amine acts in the role of a nucleophile, the second amine acts in the role of a cationic stabilization moiety as it stabilizes the cation of the Schiff base. Further rearrangement of the cation of the Schiff base to the enol or keto form is known to proceed spontaneously. The cation that forms upon nucleophilic attack is similarly stabilized (as a Schiff base is) by the structure of the nucleophile. In another aspect, the structure of the nucleophile accelerates rearrangement by stabilizing the positive charge that is acquired while the compound is in the form of a cation that formed upon nucleophilic attack.

It was discovered that this spontaneous reaction is further facilitated by dehydration, as the rate was increased in dehydrated samples. It is believed that the importance of the stabilization moiety has not been discussed in the prior art within the scope of the present application as the enhanced effect of using a nucleophile of the present disclosure has not previously been disclosed. Accordingly, one aspect of the present disclosure is that the nucleophile is of a type that provides stability to a cation of a nucleophilic base during a subsequent rearrangement. In another aspect, the nucleophile is of a type that provides stability to a cation of a nucleophilic base during a subsequent rearrangement while in a substantially dry state.

In illustrative embodiments, the nucleophile is $R_1$-Q-$R_2$, wherein Q is alkyl, cycloalkyl, heteroalkyl, or cycloheteroalkyl, each of which is optionally substituted, $R_1$ is a nucleophilic moiety, and $R_2$ is the stabilization moiety. In one embodiment, $R_1$ is selected from the group consisting of an amine, an azide, a cyanate, an isocyanate, a thiol, a disulfide, a thiocyanate, a halogen, a haloformyl, a carboxyl, a carboxylate, a hydroxyl, and an alkoxide. In another embodiment, $R_2$ is selected from the group consisting of an amine, an amide, an imine, an imide, a nitro, a nitrate, a pyridine, a phosphate, a phosphono, a hydroxyl, a hydrogen, a sulphono, a sulpho, a sulfinyl, and a sulfhydryl (thiol).

In one embodiment, the nucleophile is a primary amine. As used herein, a primary amine is an organic compound having one or more primary amine groups. Within the scope of the term primary amine are those compounds which can be modified in situ or isomerize to generate a compound having one or more primary amine groups. In one embodiment, the primary amine may be a molecule having the formula of $H_2N$-Q-R, wherein Q is an alkyl, cycloalkyl, heteroalkyl, or cycloheteroalkyl, each of which may be optionally substituted and R includes a cationic stabilization moiety selected from the group consisting of an amine, an amide, an imine, an imide, a nitro, a nitrate, a pyridine, a phosphate, a phosphono, a hydroxyl, a hydrogen, a sulphono, a sulpho, a sulfinyl, and a sulfhydryl (thiol).

In one embodiment, Q is an alkyl selected from the group consisting of $C_2$-$C_{24}$. In another embodiment, Q is an alkyl selected from the group consisting of $C_2$-$C_8$. In another embodiment, Q is an alkyl selected from the group consisting of $C_3$-$C_7$. In yet another embodiment, Q is a $C_6$ alkyl. In one embodiment, Q is selected from the group consisting of a cyclohexyl, cyclopentyl or cyclobutyl. In another embodiment, Q is a benzyl. In one embodiment, $R_1$-Q-$R_2$ is 2[(2-aminoethyl)amino]ethanol. In another embodiment of $R_1$-Q-$R_2$, each of $R_1$ and $R_2$ is thiol.

In one embodiment, $R_1$ is an amine. In a further embodiment of the above, $R_2$ is an amine, an amide, an imine, or an imide. In a further embodiment of the above, $R_2$ is an amine.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that alkyl is advantageously of limited length, including $C_1$-$C_{24}$, $C_1$-$C_8$, $C_1$-$C_6$, and $C_1$-$C_4$. It is to be further understood that alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less hydrophilicity to the compound and accordingly will have different reactivity towards the carbohydrate reactant and solubility in a binder solution.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

In illustrative embodiments, the nucleophile is a diamine, triamine, tetraamine, or pentamine. In one embodiment, the polyamine is a triamine selected a diethylenetriamine, 1-piperazineethanamine, or bis(hexamethylene)triamine. In another embodiment, the polyamine is a tetramine, for example triethylenetetramine. In another embodiment, the polyamine is a pentamine, for example tetraethylenepentamine.

One aspect of the nucleophile is that it may possess low steric hindrance. For example, Q is selected such that the nucleophile has low steric hindrance. For example, if Q is essentially linear and has a length of at least three atoms, the nucleophilic moiety and the stabilizing moiety are sufficiently spaced so that the nucleophile is able to react with the electrophile.

While not being limited to a particular theory, the stabilization moiety is so-called because it may stabilize a reaction intermediate as described herein. However, in another aspect of the present disclosure, the stabilization moiety may also serve as a reactant within the scope of the present disclosure. As such, rearrangement products existing after the reaction between the nucleophilic moiety and the carbohydrate may convert or return the stabilization moiety into a group that reacts or is capable of reacting with another carbohydrate. Accordingly, the stabilization moiety may convert or return to the form of a nucleophilic moiety and react with the carbohydrate accordingly.

In illustrative embodiments, the Q group, as described herein, can serve to isolate the two groups such that $R_1$ and $R_2$ are essentially unaffected by the chemistry occurring at the other position. As such, the Q group may or may not be serving in the capacity of a stabilization moiety. According to this theory, the advantages gained through utilization of a di-functional nucleophile are attributable primarily to the fact that a single di-functional compound can form a cross-link between two carbohydrate compounds. Because the two functional groups are linked through a Q group, upon reaction of both $R_1$ and $R_2$, the result is a higher molecular weight product than if $R_1$ and $R_2$ were not linked through the Q group. As such, the $R_1$ and $R_2$ can be selected from the group consisting of an amine, an azide, a cyanate, an isocyanate, a thiol, a disulfide, a thiocyanate, a halogen, a haloformyl, a carboxyl, a carboxylate, a hydroxyl, an alkoxide, an amide, an imine, an imide, a nitro, a nitrate, a pyridine, a phosphate, a phosphono, a hydroxyl, a hydrogen, a sulphono, a sulpho, a sulfinyl, and a sulfhydryl (thiol).

In illustrative embodiments, the Q group is of the type which enables the chemical communication between $R_1$ and $R_2$. For example, Q may enable chemical communication by enabling resonance and polarity shifts from $R_1$ to $R_2$. In other embodiments, Q may be of a length that reactions at either $R_1$ and $R_2$ cause changes to the electron distribution at the other group ($R_1$ or $R_2$). In one embodiment, the nucleophile includes a stabilization moiety and a nucleophilic moiety. In one embodiment, the nucleophilic moiety is selected from the group consisting of an amine, an azide, a cyanate, an isocyanate, a thiol, a disulfide, a thiocyanate, a halogen, a haloformyl, a carboxyl, a carboxylate, a hydroxyl, and an alkoxide. In another embodiment, the cationic stabilization moiety is selected from the group consisting of an amine, an amide, an imine, an imide, a nitro, a nitrate, a pyridine, a phosphate, a phosphono, a hydroxyl, a hydrogen, a sulphono, a sulpho, a sulfinyl, and a sulfhydryl (thiol).

In one embodiment, the nucleophile may include a polymeric polyamine. For example, polymeric polyamines within the scope of the present disclosure include chitosan, polylysine, polyethylenimine, poly(N-vinyl-N-methyl amine), polyaminostyrene and polyvinylamines. In one embodiment, the polyamine comprises a polyvinyl amine. As used herein, the polyvinyl amine can be a homopolymer or a copolymer.

While not limited to a particular theory, one aspect of the present disclosure is that the primary amine and the carbohydrate reactant are Maillard reactants that react to form a melanoidin product. FIG. 1 shows a schematic of a Maillard reaction, which culminates in the production of melanoidins. In its initial phase, a Maillard reaction involves a carbohydrate reactant, for example, a reducing sugar (note that the carbohydrate reactant may come from a substance capable of producing a reducing sugar under Maillard reaction conditions). The reaction also involves condensing the carbohydrate reactant (e.g., reducing sugar) with an amine reactant, i.e., a compound possessing an amino group. In other words, the carbohydrate reactant and the amine reactant are the melanoidin reactants for a Maillard reaction. The condensation of these two constituents produces an N-substituted glycosylamine. For a more detailed description of the Maillard reaction see, Hodge, J. E. Chemistry of Browning Reactions in Model Systems *J. Agric. Food Chem.* 1953, 1, 928-943, the disclosure of which is hereby incorporated herein by reference. The literature on Maillard reactions focuses on a melanoidins produced from amino acids. The present disclosure can be distinguished from these references in that the nucleophiles within the scope of the present disclosure also include a stabilization moiety. Common amino acids which are considered within the scope of the present disclosure include asparagine, glutamine, histidine, lysine, and arginine.

Without being bound to theory, the covalent reaction between the nucleophile and the carbohydrate reactant will be described in greater specificity. As described herein, the pathway of the present reaction is distinct from those taught in the prior art for the following reasons: (1) the present reaction may occur completely at basic pH, (2) the nucleophile is di-functional having a nucleophilic moiety and a stabilization moiety, (3) the nucleophile, through its di-functionality or another unrecognized phenomena, exhibits a lower activation energy within the scope of the reaction which results in an unexpected increase in reaction rate and/or a decrease in the temperature at which the reaction will proceed.

In illustrative embodiments, the first step in the formation of high molecular weight polymers from a nucleophile and a carbohydrate reactant is the condensation of the carbohydrate reactant and the nucleophile. Evidence indicates that the conditions described herein are especially suitable for driving this reaction to completion. First, it is believed that the alkalinity of the binder solution drives the condensation. For example, it has been shown that sugars and nucleophiles such as amines undergo browning in aqueous solution in proportion to the basic strength of the amines employed or the pH of the solution. In this example, it is believed that the N-substituted glycosylamines remain undissociated in aqueous solutions to appreciable extents. Thus, the irreversible transformations that the undissociated molecules undergo must be considered. While it is known that the condensation reaction is reversible, we discovered that this reaction can be further driven to completion, in accordance with Le Chatelier's principle by the concurrent dehydration of the binder solution. As such, it was established that initially a primary constituent of the uncured binder composition was the condensation products of the nucleophile and the carbohydrate.

Figure 2:
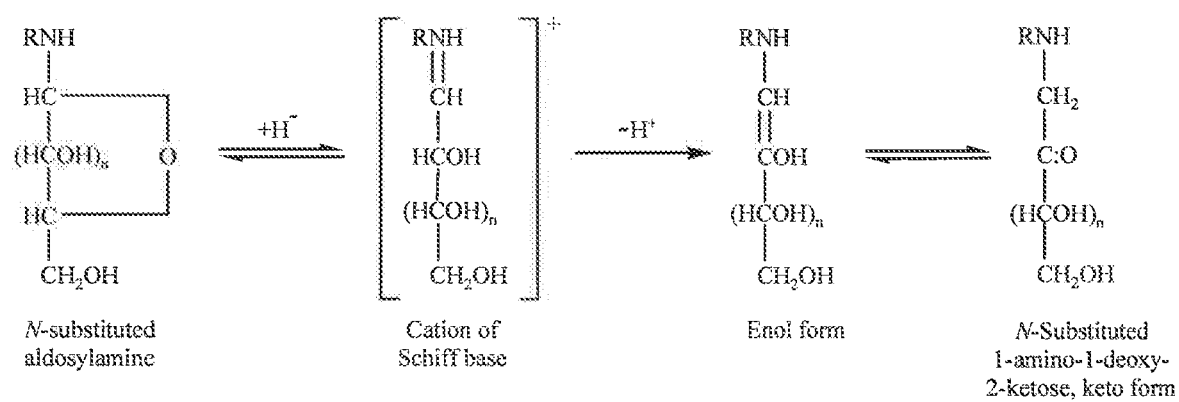
FIG. 2 shows a schematic of a representative Amadori rearrangement.

The second step in the conversion of the binder reactants to high molecular weight polymer products may be a rearrangement. An exemplary rearrangement is shown as a schematic of a Amadori rearrangement in FIG. 2. Referring to FIG. 2, the N-glycosyl derivatives of the representative amines are in equilibrium with the cation of a Schiff base. While this equilibrium favors the N-glycosylamine, further rearrangement of the cation of a Schiff base to the enol or keto form is known to proceed spontaneously. It was discovered that this spontaneous reaction is further facilitated by dehydration, as the rate was increased in dehydrated samples. One aspect of the present disclosure is that the structure of a nucleophile specifically accelerates this rearrangement by stabilizing the positive charge that is acquired while the compound is in the form of a cation of a Schiff base. It is believed that this stabilization effect has not been discussed in the prior art or the literature as the enhanced effect of using a nucleophile as such within the scope of the present disclosure has not previously been disclosed. Accordingly, one aspect of the present disclosure is that the nucleophile is of a type that provides stability to a cationic base during a rearrangement. In another aspect, the nucleophile is of a type that provides stability to a cationic base during a rearrangement while in a substantially dry state.

Another aspect of the present disclosure is that the carbohydrate structure is also believed to influence the kinetics of the rearrangement. Specifically, it is known when the C-2 hydroxyl of a crystalline N-substituted glycosylamine was unsubstituted, the compound was slowly transformed during storage to the rearrangement product. However, if the C-2 hydroxyl was substituted, then the rearrangement was substantially inhibited. Accordingly, one aspect of the present disclosure is that a carbohydrate of the present disclosure is unsubstituted at the hydroxyl adjacent to the ketone or aldehyde.

In illustrative embodiments, the molar ratio of the carbohydrate reactant to the nucleophile is in the range of about 1:1 to about 30:1. In another embodiment, the molar ratio of the carbohydrate reactant to the nucleophile is in the range of about 2:1 to about 10:1. In yet another embodiment, the molar ratio of the carbohydrate reactant to the nucleophile is in the range of about 3:1 to about 6:1. According to one aspect, the cure rate is a function of the molar ratio of the carbohydrate reactant to the primary polyamine. According to this function, it was established that as the ratio decreased, the cure rate increased; thus the cure time decreased. Accordingly, the one aspect of the present disclosure is that the cure time is directly related to the molar ratio of the carbohydrate reactant to the polyamine provided that other parameters are held equivalent. In another aspect, the binder cure time is reduced to the cure time of a comparable phenol formaldehyde binder composition when the molar ratio of the carbohydrate reactant to the nucleophile is equal to about 6:1. Accordingly, in one embodiment, a binder according to the present disclosure has a cure rate exceeding a comparable phenol formaldehyde binder system when the carbohydrate reactant to nucleophile molar ratio is in the range of about 2:1 to about 6:1.

Another aspect of the reaction, as described herein, is that initially the aqueous reactant solution (which may be dehydrated and used as a binder) has an alkaline pH. One aspect of the present disclosure is that the alkaline binder solution is less corrosive towards metal than acidic solution. Accordingly, one feature of the present disclosure which overcomes a substantial barrier to the industry is that the binder described herein has low corrosivity towards the manufacturing equipment which may be used to produce materials which include the present binder because of the alkaline binder composition. One distinguishing feature of the present disclosure over other recently described carbohydrate binder systems (e.g. U.S. Published Application No. 2007/0027283), is that the reaction does not necessarily proceed through an acidic pathway. Rather, one aspect of the present disclosure is that the uncured binder may have an alkaline pH throughout the course of the chemical reaction which leads to the formation of the cured binder. As such, the uncured binder, throughout its use and storage does not present a corrosion risk. In illustrative embodiments, an aqueous extract of the cured binder has a pH in the range of about 5 to about 9. Furthermore, an aqueous extract of the polymeric product is essentially colorless.

In illustrative embodiments, a method of making a collection of matter bound with a polymeric binder comprises preparing a solution containing reactants for producing the polymeric binder and a solvent, wherein the reactants include a carbohydrate reactant and a nucleophile; disposing the solution onto the collection of matter; volatilizing the solvent to form an uncured product, and subjecting the uncured product to conditions that cause the carbohydrate reactant and the nucleophile to polymerize to form the polymeric binder.

In illustrative embodiments, the collection of matter includes insulating fibers. In one embodiment, a fiber insulation product is described which includes insulating fibers and a binder. As used herein, the term "insulating fiber," indicates heat-resistant fibers suitable for withstanding elevated temperatures. Examples of such fibers include, but are not limited to, mineral fibers (glass fibers, slag wool fibers, and rock wool fibers), aramid fibers, ceramic fibers, metal fibers, carbon fibers, polyimide fibers, certain polyester fibers, and rayon fibers. Illustratively, such fibers are substantially unaffected by exposure to temperatures above about 120° C. In one embodiment, the insulating fibers are glass fibers. In yet another embodiment, the mineral fibers are present in the range from about 70% to about 99% by weight.

In illustrative embodiments, the collection of matter includes cellulosic fibers. For example, the cellulosic fibers may be wood shavings, sawdust, wood pulp, or ground wood. In yet another embodiment, the cellulosic fibers may be other natural fibers such as jute, flax, hemp, and straw. The binder disclosed herein may be used as in the place of the binder described in Published PCT application WO 2008/089847, which is incorporated herein by reference in its entirety. In one embodiment, a composite wood board comprising wood particles and a binder is disclosed. In another embodiment, the composite wood board is formaldehyde free. In one embodiment, the composite wood board has a nominal thickness range of greater than 6 mm to 13 mm, and has a modulus of elasticity (MOE) of at least about 1050 N/mm$^2$, a bending strength (MOR) of at least about 7 N/mm$^2$, and an internal bond strength (IB) of at least 0.20 N/mm$^2$. In another embodiment, the composite wood board has a nominal thickness range of greater than 6 mm to 13 mm, and has a bending strength (MOR) of at least about 12.5 N/mm$^2$, and an internal bond strength (TB) of at least 0.28 N/mm$^2$. In another embodiment, the composite wood board has a nominal thickness range of greater than 6 mm to 13 mm, and has a modulus of elasticity (MOE) of at least about 1800 N/mm$^2$, a bending strength (MOR) of at least about 13 N/mm$^2$, and an internal bond strength (TB) of at least 0.40 N/mm$^2$. In another embodiment, the composite wood board has a modulus of elasticity (MOE) of at least about 1800 N/mm$^2$. In another embodiment, the composite wood board has a modulus of elasticity (MOE) of at least about 2500 N/mm$^2$. In another embodiment, the composite wood board has a bending strength (MOR) of at least about 14 N/mm$^2$. In yet another embodiment, the composite wood board has a bending strength (MOR) is at least about 18 N/mm$^2$. In one embodiment, the composite wood board has an internal bond strength (TB) of at least 0.28 N/mm$^2$. In yet another embodiment, the composite wood board has an internal bond strength (TB) is at least 0.4 N/mm$^2$. In yet another embodiment, the composite wood board swells less than or equal to about 12%, as measured by a change in thickness, after 24 hours in water at 20° C. In another embodiment, the composite wood board has a water absorption after 24 hours in water at 20° C. of less than or equal to about 40%.

In illustrative embodiments the composite wood board is a wood particleboard, an orientated strandboard, or a medium density fiberboard. In one embodiment, the binder comprises from about 8% to about 18% by weight (weight of dry resin to weight of dry wood particles) of the composite wood board. In another embodiment, the composite wood board further comprises a wax. In yet another embodiment, the composite wood board comprises from about 0.1% to about 2% wax by weight of the composite wood board. In illustrative embodiments, the method of making a collection of matter bound with a polymeric binder may further include preparing a solution by adding an amount of a carbohydrate reactant and an amount of a nucleophile so a molar ratio is in the range of about 2:1 to about 10:1. In one embodiment, preparing the solution includes adding the carbohydrate reactant and the polyamine to an aqueous solution. In another embodiment, preparing the solution includes adjusting the pH of the solution to within the range of about 8 to about 12. In yet another embodiment, the method of making a collection of matter bound with a polymeric binder may further comprise packaging the uncured product in a packaging material suitable for storage.

In illustrative embodiments, the present disclosure relates to a composition comprising a collection of matter and a binder, the binder comprising polymeric products of a reaction between a carbohydrate reactant and a nucleophile, the polymeric products being substantially water insoluble. In one embodiment, the collection of matter includes mineral fibers, aramid fibers, ceramic fibers, metal fibers, carbon fibers, polyimide fibers, polyester fibers, rayon fibers, or cellulosic fibers. For example, cellulosic fibers may include wood shavings, sawdust, wood pulp, and/or ground wood. In one embodiment, the collection of matter includes sand or other inorganic particulate matter. In one embodiment, the collection of matter is coal particulates. In one embodiment, the carbohydrate reactant is selected from the group consisting of dextrose, xylose, fructose, dihydroxyacetone, and mixtures thereof. In one embodiment, the nucleophile is $R_1$-Q-$R_2$, wherein Q is alkyl, cycloalkyl, heteroalkyl, or cycloheteroalkyl, each of which is optionally substituted, $R_1$ is a nucleophilic moiety, and $R_2$ is a stabilization moiety.

In another embodiment, the composition further comprises a silicon-containing compound. In one embodiment the silicon-containing compound is a functionalized silylether or a functionalized alkylsilylether, such as for example, an amino-functionalized alkylsilylether. For example, in one embodiment, the silicon-containing compound may be gamma-aminopropyltriethoxysilane, gamma-glycidoxypropyltrimethoxysilane, or aminoethylaminopropyltrimethoxysilane, or a mixture thereof. In another embodiment, the silicon-containing compound may be an aminofunctional oligomeric siloxane. In another embodiment, the composition comprises a corrosion inhibitor selected from the group consisting of dedusting oil, monoammonium phosphate, sodium metasilicate pentahydrate, melamine, tin (II)oxalate, and a methylhydrogen silicone fluid emulsion.

In further illustrative embodiments, the binder may be disposed upon a collection of fibers, substantially dehydrated, packaged, and then stored or sold to another party. An uncured product sold to another party for use in further manufacturing processes may be referred to as "ship-out uncured." An uncured product stored for use in further manufacturing processes may be referred to as "plant uncured." In selling or storing this type of product, it is packaged in suitable containers or bags.

In illustrative embodiments, a packaged uncured fiber product comprises an uncured binder composition and a collection of fibers, wherein (i) the uncured binder composition is in contact with the collection of fibers consolidating the collection of fibers and (ii) the uncured binder composition in contact with the collection of fibers is packaged in a suitable packaging material. In one embodiment, the amount of moisture in the uncured binder composition may be in a range from about 1% to about 15% by weight based on a total weight of the product. In yet another embodiment, the suitable packaging material may be capable of maintaining the amount of moisture in the uncured binder composition to within about 20% of an original moisture level for a period of one week at an ambient temperature and an ambient pressure. In one embodiment, the packaged uncured fiber product comprises from about 3% to about 30% by weight of the uncured binder composition based on weight of the packaged uncured fiber product without considering the weight of the suitable packaging material. In one embodiment, the packaged uncured fiber product comprises from about 60 to about 97% by weight fibers based on weight of the packaged uncured fiber insulation product without considering the weight of the suitable packaging material.

One aspect of the present disclosure is that the binder described herein is unexpectedly useful in applications ship-out uncured and plant uncured applications. Specifically, ship-out uncured products and plant uncured products are provided with an uncured binder so that the curing can occur at a later time and in a later place. In the case of ship-out uncured, the curing temperature and time are properties of the product which are of great importance to the customers. Specifically, the cure temperatures must be sufficiently low such that the product can be cured using their existing equipment. Furthermore, the cure time must be sufficiently short such that the cycle time for curing the products remains low. Within this industry, the manufacturing equipment and acceptable cycle times have been established for uncured products comprising phenol formaldehyde type resins. Therefore, sufficiently low cure temperatures are those cure temperatures suitable for curing a comparable phenol formaldehyde type product. Similarly, sufficiently low cycle times are those cycle times which would be routine for curing a comparable phenol formaldehyde type product. One of ordinary skill in the art will appreciate that neither cure time nor cure temperature can be set forth as definite quantities because the specific applications may have dramatically different parameters. However, it is well understood that the cure time and cure temperatures of a model system provide sufficient representative information regarding the kinetics of the underlying chemical curing reaction so that reliable predictions of binder performance in the various applications can be made.

In illustrative embodiments, the cure time and the cure temperature of the binder is equal to or less than a comparable phenol formaldehyde binder composition. In one embodiment, the cure time of the binder is less than the cure time of a comparable phenol formaldehyde binder composition. In another embodiment, the cure temperature of the binder is less than the cure temperature of a comparable phenol formaldehyde binder composition. As used herein, a comparable phenol formaldehyde binder composition is like that described according to U.S. Pat. No. 6,638,882, which patent is hereby incorporated by reference herein in its entirety.

As discussed below, various additives can be incorporated into the binder composition. These additives give the binders of the present invention additional desirable characteristics. For example, the binder may include a silicon-containing coupling agent. Many silicon-containing coupling agents are commercially available from the Dow-Corning Corporation, Evonik Industries, and Momentive Performance Materials. Illustratively, the silicon-containing coupling agent includes compounds such as silylethers and alkylsilyl ethers, each of which may be optionally substituted, such as with halogen, alkoxy, amino, and the like. In one variation, the silicon-containing compound is an amino-substituted silane, such as, gamma-aminopropyltriethoxy silane (SILQUEST A-1101; Momentive Performance Materials, Corporate Headquarters: 22 Corporate Woods Boulevard, Albany, N.Y. 12211 USA). In another variation, the silicon-containing compound is an amino-substituted silane, for example, aminoethylaminopropyltrimethoxy silane (Dow Z-6020; Dow Chemical, Midland, Mich.; USA). In another variation, the silicon-containing compound is gamma-glycidoxypropyltrimethoxysilane (SILQUEST A-187; Momentive). In yet another variation, the silicon-containing compound is an aminofunctional oligomeric siloxane (HYDROSIL 2627, Evonik Industries, 379 Interpace Pkwy, Parsippany, N.J. 07054).

The silicon-containing coupling agents are typically present in the binder in the range from about 0.1 percent to about 1 percent by weight based upon the dissolved binder solids (i.e., about 0.05% to about 3% based upon the weight of the solids added to the aqueous solution). In one application, one or more of these silicon-containing compounds can be added to the aqueous binder solution. The binder is then applied to the material to be bound. Thereafter, the binder may be cured if desired. These silicone containing compounds enhance the ability of the binder to adhere to the matter the binder is disposed on, such as glass fibers Enhancing the binder's ability to adhere to the matter improves, for example, its ability to produce or promote cohesion in non- or loosely-assembled substance(s).

In another illustrative embodiment, a binder of the present invention may include one or more corrosion inhibitors. These corrosion inhibitors prevent or inhibit the eating or wearing away of a substance, such as, metal caused by chemical decomposition brought about by an acid. When a corrosion inhibitor is included in a binder of the present invention, the binder's corrosivity is decreased as compared to the corrosivity of the binder without the inhibitor present. In one embodiment, these corrosion inhibitors can be utilized to decrease the corrosivity of the glass fiber-containing compositions described herein. Illustratively, corrosion inhibitors include one or more of the following, a dedusting oil, or a monoammonium phosphate, sodium metasilicate pentahydrate, melamine, tin(II) oxalate, and/or methylhydrogen silicone fluid emulsion. When included in a binder of the present invention, corrosion inhibitors are typically present in the binder in the range from about 0.5 percent to about 2 percent by weight based upon the dissolved binder solids. One aspect of the present disclosure is that the need for corrosion inhibiting additives is greatly reduced by the alkalinity of the binder solution and the substantially dehydrated uncured binder. In one embodiment, the binder is free from corrosion inhibitors and the corrosivity of the binder solution is within the acceptable range.

In illustrative embodiments, the binder may further include a non-aqueous moisturizer. The non-aqueous moisturizer may include one or more polyethers. For example, the non-aqueous moisturizer may include an ethylene oxide or propylene oxide condensates having straight and/or branched chain alkyl and alkaryl groups. In one embodiment, the non-aqueous moisturizer includes a polyethylene glycol, a polypropylene glycol ether, a thioether, a polyoxyalkylene glycol (e.g., Jeffox TP400®), a dipropylene glycol, and/or a polypropylene glycol (e.g., Pluriol P425® or Pluriol 2000®). In one embodiment, the non-aqueous moisturizer comprises a polyoxyalkylene glycol or a polypropylene glycol. In another embodiment, the non-aqueous moisturizer includes a compound based on a polyhydroxy compound (e.g., a partially or fully esterified polyhydroxy compound). In another embodiment, the non-aqueous moisturizer includes a polyhydroxy based on a glycerine, a propylene glycol, an ethylene glycol, a glycerine acetate, a sorbitol, a xylitol or a maltitol.

In another embodiment, the non-aqueous moisturizer includes other compounds having multiple hydroxyl groups based on tetrahydrofuran, a caprolactone, and/or alkylphenoxypoly(ethyleneoxy)ethanols having alkyl groups containing from about 7 to about 18 carbon atoms and having from about 4 to about 240 ethyleneoxy units. For example, the non-aqueous moisturizer may include a heptylphenoxypoly(ethyleneoxy)ethanol and/or a nonylphenoxypoly(ethyleneoxy)ethanol. In another embodiment, the non-aqueous moisturizer includes a polyoxyalkylene derivative of hexitol such as a sorbitan, sorbide, mannitan, and/or a mannide. In yet another embodiment, the non-aqueous moisturizer may include a partial long-chain fatty acids ester, such as a polyoxyalkylene derivative of sorbitan monolaurate, sorbitan monopalmitate, sorbitan monostearate, sorbitan tristearate, sorbitan monooleate, and/or sorbitan trioleate.

In illustrative embodiments, the non-aqueous moisturizer includes a condensate of ethylene oxide with a hydrophobic base, the base being formed by condensing propylene oxide with propylene glycol. In one embodiment, the non-aqueous moisturizer includes a sulfur containing condensate, such as those prepared by condensing ethylene oxide with a higher alkyl mercaptan (e.g., nonyl, dodecyl, tetradecyl mercaptan, or alkylthiophenols having about 6 to about 15 carbon atoms in the alkyl group). In another embodiment, the non-aqueous moisturizer includes an ethylene oxide derivative of a long-chain carboxylic acid, such as lauric, myristic, palmitic, or oleic acid. In yet another embodiment, the non-aqueous moisturizer includes an ethylene oxide derivative of a long-chain alcohol such as octyl, decyl, lauryl, or cetyl alcohol. In another embodiment, the non-aqueous moisturizer includes an ethylene oxide/tetrahydrofuran copolymer or an ethylene oxide/propylene oxide copolymer.

The following examples illustrate specific embodiments in further detail. These examples are provided for illustrative purposes only and should not be construed as limiting the invention or the inventive concept to any particular physical configuration in any way.

EXAMPLES

Example 1: A solution of 50 g dextrose (0.278 mol), 50 g hexamethylenediamine (0.431 mol) dissolved in 566.6 g deionized water (15% solids solution, pH 11.9) was heated to the boiling point of the solution. A brownish water insoluble polymer was observed as a precipitate in the reaction vessel.

Example 2: From the above solution of 50 g dextrose (0.278 mol), 50 g hexamethylenediamine (0.431 mol) dissolved in 566.6 g deionized water (15% solids solution, pH 11.9), 2 g of the binder solution was applied on a filter pad which is placed in a Moisture Balance and heated for 15 min at 120° C. A brownish water insoluble polymer formed on the filter pad. An extraction of the cured filter pad using 100 g of deionized water is essentially colorless and has a pH of 6.8.

Example 3: A solution of 85 g dextrose (0.472 mol), 15 g hexamethylenediamine (0.129 mol) dissolved in 566.6 g deionized water (15% solids solution, pH 10.8) was prepared. 2 g of the binder solution was applied on a filter pad which is placed in a Moisture Balance and heated for 15 min at 140° C. A brownish water insoluble polymer formed on the filter pad. An extraction of the cured filter pad using 100 g of deionized water is essentially colorless and has a pH of 6.8.

Example 4: A solution of 95 g dextrose (0.528 mol), 5 g hexamethylenediamine (0.043 mol) dissolved in 566.6 g deionized water (15% solids solution) was prepared. 2 g of the binder solution was applied on a filter pad which is placed in a Moisture Balance and heated for 15 min at 180° C. A brownish water insoluble polymer formed on the filter pad. An extraction of the cured filter pad using 100 g of deionized water is essentially colorless and has a pH of 6.8.

Comparative Example 1: A solution of 180 g dextrose (1 mol) dissolved in 1020 g deionized water (15% solids solution) was prepared. 2 g of the binder solution was applied on a filter pad which is placed in a Moisture Balance and heated for 15 min at 180° C. A water insoluble polymer was not formed on the filter pad. The resulting heat treated binder was essentially fully water soluble.

Cure Rate and Cure Time: Square Fiberglass mats (13"×13") with a weight of 44 g (corresponding to 34.5 g/ft$^2$) were impregnated with a binder containing 15% solids. Excess of binder is removed by vacuum suction, and the moist mat is dried for at least 12 hours at 90° F. in an oven (recirculation).

The dried mat is cut in four squares of the same dimension. The squares are stacked on top of each other, and at least one thermocouple connected to a recorder (i.e. oven mole) is placed in the middle of the stack between the 2$^{nd}$ and 3' layer.

A mold press with temperature controlled platen is heated to 400° F. (204° C.). The sample with the prepared thermocouple is placed in the middle of the platen, and pressed to a thickness of ⅝" for a predefined time (i.e. 3.5 min, 4.0 min, 5.0 min, 6.0 min, 15 min).

Figure 3:
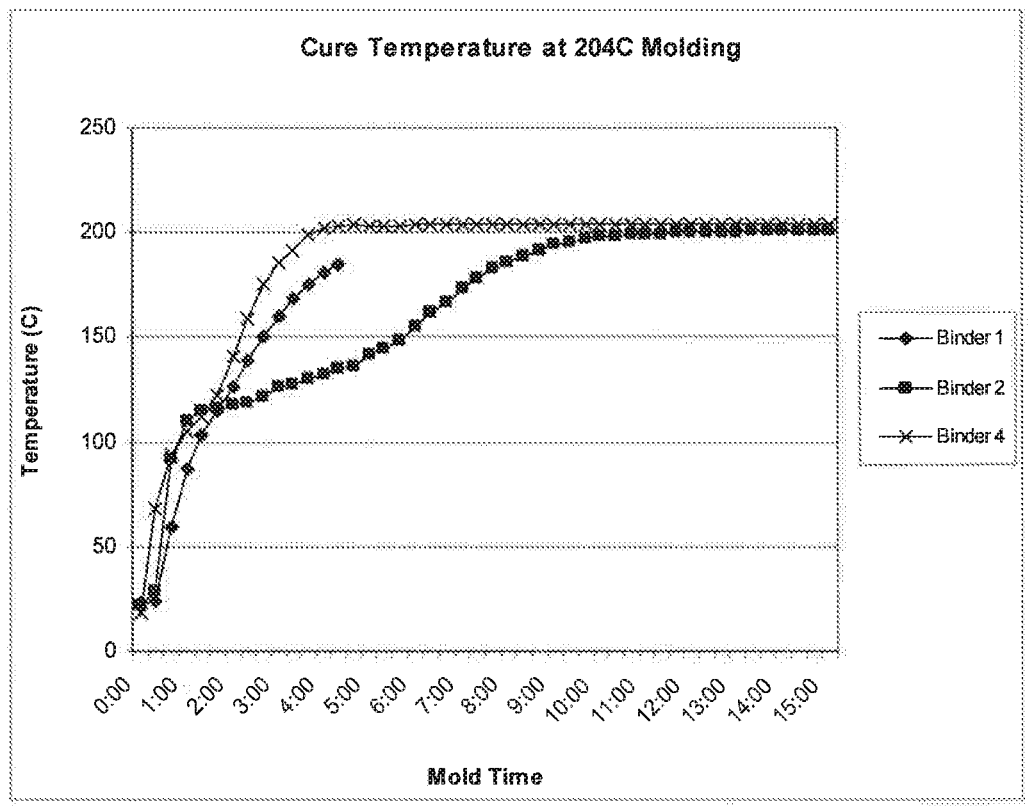
FIG. 3 shows the cure temperature profile (Y-axis in ° C.) of the center of a fiberglass mat sample for different binders during a heat molding cycle (X-axis in minutes of mold time) using a mold press with a temperature controlled platen at 204° C. Binder 1 (♦) is a phenol formaldehyde binder (Comparative Example 2); Binder 2 (■) is a carbohydrate—inorganic acid binder (Comparative Example 3); and Binder 3 (X) is a dextrose—ammonia—hexamethylene diamine (HMDA) binder (Example 5).

Each molded sample was evaluated for the degree of cure by testing evenness of the surfaces, water hold-up, and extract. A sample was deemed to be cured when the surfaces are smooth without any "bumps", the sample does not noticeably weaken when immersed in water, and no significant extract color is formed when immersing the sample in water. The temperature profile of the center of the sample is measured during the molding cycle and is shown in FIG. 3.

Comparative Example 2: Phenol Formaldehyde Binder.
Composition based on dry solids:
  2.41 parts Ammonium Sulfate
  1.08 part of Ammonia
  0.21 parts Silane A1101
  96.3% phenol formaldehyde-Resin:Urea Premix (70:30)
Comparative Example 2 is referred to as Binder 1 within FIG. 3.

Comparative Example 3: Carbohydrate-Inorganic Acid Binder.
Composition based on dry solids:
  81.59 parts Dextrose
  17.09 parts Ammonium Sulfate
  1 part of Ammonia
  0.3 parts Silane A1101
Comparative Example 3 is referred to as Binder 2 within FIG. 3.

Example 5

Composition based on dry solids:
  80.94 parts Dextrose and Ammonia solution (an aqueous solution containing 2 mol/liter Dextrose and 2 mol/liter Ammonia)
  19.06 parts Hexamethylenediamine
Example 5 is referred to as Binder 4 within FIG. 3.

It was determined that the time required to achieve full cure of a binder within the scope of the present disclosure is less than that of 3 comparative example binder systems having diverse chemistries. This model system illustrates that the cure time, providing that other variables are kept constant, is dependent on the chemistry of the binder system. The chemistry of an illustrative binder composition within the scope of the present disclosure achieves improved cure times in comparison to these other exemplary systems. The results are shown following:

| Binder | Molding Time to achieve full cure |
|---|---|
| Comparative Ex. 2 - Binder 1 | Minimum of 240 seconds |
| Comparative Ex. 3 - Binder 2 | Minimum of 300 seconds |
| Ex. 5 - Binder 4 | Cured at 210 seconds |

Referring now to FIG. 3, shown is the temperature profile characteristic for each of binders 1, 2, and 4. It was noted that the temperature profile is characteristic for each binder. It was not established that the cure rate and cure time is not characteristic of the cure temperature profile. However, the cure temperature profile helps to understand and predict cure rate and cure time. Specifically, Comparative Example 3 required the greatest cure time and similarly the cure temperature profile required the greatest amount of time to asymptotically maximize. Similarly, Example 5 required the least amount of time to asymptotically maximize and demonstrated the shortest cure time.

Carbohydrate Reactant: Polyamine Ratio Effect on Cure Cycle Time. Wet Laid Mats (WLM) were made with varying ratios of dextrose monohydrate (DMH) to Hexamethylenediamine (HMDA). The weight ratios tested include 75/25, 85/15, and 92/8 respectively.

A 15% Dextrose-HMDA Binder was applied to 5 WLM's. The following binder compositions were prepared:

| | Example 6 DMH/HMDA 75/25 | Example 7 DMH/HMDA 85/15 | Example 8 DMH/HMDA 92/8 |
|---|---|---|---|
| Water | 1677.45 g | 1677.45 g | 1677.45 g |
| DMH | 246.78 g | 279.68 g | 302.72 g |
| HMDA | 74.77 g | 44.86 g | 23.93 g |
| Silane | 1.00 g | 1.00 g | 1.00 g |

The mats are prepared in 13"×13" pieces, with a thickness of ⅜". The press used to mold the mats is set at 400° F. Once the sample is molded it is approximately ⅝" thick. A temperature profile was first determined in a 15 minute interval. The next sample was pressed for 4 minutes; this is the time it takes to cure a comparable phenol formaldehyde binder composition (results not shown). The experiments were repeated with varying cure times until the minimum time required to cure each composition was determined. The extent to which each binder had cured was determined based on weight. The following results were determined:

| | Cure Cycle Time |
|---|---|
| Example 6 | 2:30 min. |
| Example 7 | 4 min. |
| Example 8 | 8 min. |

As described above, comparable phenol formaldehyde based product (e.g. Comparative Example 2) cures with a 4 minute cycle time. Furthermore, a comparable carbohydrate based binder (e.g. Comparative Example 3) cures with a 5 minute cycle time. These results indicate that a binder within the scope of the present disclosure with a carbohydrate reactant to primary polyamine of 85/15 or lower cures at a comparable or faster rate than the phenol formaldehyde based product. Further experiments showed that the cure temperature can be lowered in products having a shorter cure time to achieve equivalent cure times at lower temperatures. The results obtained agreed in principle to our expectations based on the Arrhenius equation.

In addition to those examples described in detail, the following examples were made to ensure that the carbohydrate reactant and polyamine may comprise a wide range of alternatives.

| Ex. | Polyamine | Carbohydrate Reactant | Binder Formed |
|---|---|---|---|
| 9 | hexamethylenediamine | dextrose | Yes |
| 10 | ethylenediamine | dextrose | Yes |
| 11 | diethylenetriamine | dextrose | Yes |
| 12 | hexamethylenediamine | high fructose corn syrup | Yes |
| 13 | hexamethylenediamine | sucrose | Yes |
| 14 | octamethylenediamine | dextrose | Yes |
| 15 | tetramethylenediamine | dextrose | Yes |

Further Dextrose—Nucleophile Examples

Example 16: A suspension of 56.08 g deionized water, 7.15 g dextrose monohydrate, and 3.5 g 1,12-diaminododecane was acidified with 11 N HCl to pH 1.0, and heated to 70° C. under agitation resulting into a clear, colorless solution. The solution forms a thermoset, water insoluble polymer at 160° C. (Test condition: 2 g binder solution is applied on a filter pad which is placed in a Moisture Balance. The filter pad is heated for 15 min at 160° C.) An extract of the cured filter pad with 100 g of deionized water is essentially colorless.

Example 17: A solution of 8.25 g dextrose monohydrate, and 2.50 g 1,5-diamino-2-methylpentane (Dytek A, Invista) dissolved in 56.08 g deionized water forms a thermoset, water insoluble polymer at 160° C. (Test condition: 2 g binder solution is applied on a filter pad which is placed in a Moisture Balance. The filter pad is heated for 15 min at 160° C.) An extract of the cured filter pad with 100 g of deionized water is essentially colorless.

Example 18: A solution of 8.03 g dextrose monohydrate, and 2.70 g N-(3-aminopropyl)-1,3-propanediamine dissolved in 56.08 g deionized water forms a thermoset, water insoluble polymer at 200° C. (Test condition: 2 g binder solution is applied on a filter pad which is placed in a Moisture Balance. The filter pad is heated for 15 min at 200° C.) An extract of the cured filter pad with 100 g of deionized water has a slight yellowish color.

Example 19: A solution of 3 g dextrose (0.016 mol) and 0.5 g hexamethylenediamine (0.004 mol) dissolved in 9 mL deionized water was prepared. This reaction mixture was heated at 100° C. for 1 hour before 0.7 g of dithiothreitol (0.004 mol) was added to the mixture which was dropped on a filter pad, this filter pad was heated at 125° C. A brownish water insoluble polymer was formed on the filter pad.

Example 20: A solution of 3 g dextrose (0.016 mol), 0.5 g hexamethylenediamine (0.004 mol) dissolved in 9 mL deionized water was prepared. This reaction mixture was heated at 100° C. for 1 hour before 0.52 g of butanedithiol (0.004 mol) was added to the mixture which was dropped on a filter pad, this filter pad was heated at 125° C. A brownish water insoluble polymer was formed on the filter pad.

Procedure for analyzing a binder sample with gas pyrolysis. Approximately 10 g of a cured product having the binder thereon is placed in a test tube, which tube is then heated to 1000° F. for 2.5 minutes at which time the headspace is sampled and analyzed by gas chromatography/mass spectrometry (GC/MS) under the following conditions: Oven, 50° C. for one minute–10° C./minute to 300° C. for 10 minutes; Inlet, 280° C. splitless; Column, HP-5 30 mm×0.32 mm×0.25 um; Column flow, 1.11 mL/minute Helium; Detector, MSD 280° C.; Injection volume, 1 mL; Detector mode, scan 34-700 amu; Threshold, 50; and Sampling Rate, 22 scans/second. A computer search of the mass spectrum of a chromatographic peak in the sample is made against the Wiley library of mass spectra. The best match is reported. A quality index (closeness of match to the library spectra) ranging from 0 to 99 is generated. Only the identity of peaks with a quality index of greater than or equal to 90 is reported.

The following table provides representative pyrolysis data that one expects from the GC/MS analysis of gaseous compounds produced during pyrolysis of a melanoidin based binder composition.

| Retention Time (min) | Tentative Identification | % Peak Area |
| --- | --- | --- |
| 1.15 | 2-cyclopenten-1-one | 10.67 |
| 1.34 | 2,5-dimethyl-furan | 5.84 |
| 3.54 | furan | 2.15 |
| 3.60 | 3-methyl-2,5-furandione | 3.93 |
| 4.07 | phenol | 0.38 |
| 4.89 | 2,3-dimethyl-2-cyclopenten-1-one | 1.24 |
| 5.11 | 2-methyl phenol | 1.19 |
| 5.42 | 4-methyl phenol | 2.17 |
| 6.46 | 2,4-dimethyl-phenol | 1.13 |
| 10.57 | dimethylphthalate | 0.97 |
| 17.89 | octadecanoic acid | 1.00 |
| 22.75 | erucylamide | 9.72 |

Following is a listing of the species observed in the pyrolysis gas chromatography mass spectrometry (Py GC-MS) of a binder sample prepared using hexamethylenediamine as the polyamine component. The pyrolysis was carried out at 200° C., 300° C., and 770° C. Fingerprinting shows a very significant peak which corresponds to acetic acid in the mass chromatogram at both 200° C. and 300° C., which was not seen in a sample made using dextrose and ammonium sulfate (see Comparative Example 3), in which the significant volatile was $SO_2$, particularly at 300° C. At 770° C., the peaks observed, in order of increasing retention time were assigned as follows: A: Co-eluting $C_5H_{10}$, $C_5H_{12}$, acetone, possibly low mw acetic acid ester; B: $C_5H_8$ diene; C: $C_5H_8$ diene; D: likely a pentanol; E: $C_6H_{12}$–a methyl pentene; F: hexane; G: methylcyclopentane; H: a cyclohexadiene; I: $C_6H_{10}$–probably a methylcyclopentane; J: benzene; K: acetic acid; L: cyclohexene; M: probably nonanol; N: 2-methyl-3-pentanone; O: 2,5-dimethylfuran; P: $C_7H_{10}$+unassigned co-elute; Q: pyridine+unassigned co-elute; R: toluene; S: possibly decenal+unassigned co-elute; T: 2-ethyl-5-methylfuran; U: a methyl pyridine; V: a methyl pyrrole; W: a xylene; X: unassigned–with alcohol functionality; Y: unassigned; Z: a xylene+unassigned co-elute; AA: unassigned; AB: a dimethyl pyrrole; AC: a dimethyl pyridine; AD: a dimethyl pyridine; AE: unassigned; AF: unassigned; AG: an ethyl methyl pyrrole+unassigned co-elute; AI: an unassigned but distinct mass spectrum (N-containing), pyrrole related; AJ: an unassigned but distinct mass spectrum (N-containing), possibly an acetamide; AK: an unassigned but distinct mass spectrum (N-containing), pyrrole related; AL: an unassigned but distinct mass spectrum (N-containing), pyrrole related; AM: an unassigned but distinct mass spectrum (N-containing), pyrrole related. The distinct mass spectra seen from peaks AI to AM are not seen in the data of prior binders not having the polyamine component.

Procedure for evaluating dry and weathered tensile strength. When evaluated for their dry and "weathered" tensile strength, glass bead-containing shell bone compositions prepared with a given binder provide an indication of the likely tensile strength and the likely durability, respectively, of a fiberglass product prepared with that particular binder. Predicted durability is based on a shell bone's weathered tensile strength: dry tensile strength ratio. Shell bones are prepared, weathered, and tested as follows, for example, for a hexamethylenediamine-dextrose binder mixture.

A shell bone mold (Dietert Foundry Testing Equipment; Heated Shell Curing Accessory, Model 366, and Shell Mold Accessory) is set to a desired temperature, generally 425° F., and allowed to heat up for at least one hour. While the shell bone mold is heating, approximately 100 g of an aqueous binder (generally 15% in binder solids) is prepared (e.g. as described in Example 7). Using a large glass beaker, 727.5 g of glass beads (Quality Ballotini Impact Beads, Spec. AD, US Sieve 70-140, 106-212 micron-#7, from Potters Industries, Inc.) are weighed by difference. The glass beads are poured into a clean and dry mixing bowl, which bowl was mounted onto an electric mixer stand. Approximately 75 g of aqueous binder is poured slowly into the glass beads in the mixing bowl. The electric mixer is then turned on and the glass beads/binder mixture is agitated for one minute. Using a large spatula, the sides of the whisk (mixer) are scraped to remove any clumps of binder, while also scraping the edges wherein the glass beads lay in the bottom of the bowl. The mixer is then turned back on for an additional minute, and then the whisk (mixer) is removed from the unit, followed by removal of the mixing bowl containing the glass beads/binder mixture. Using a large spatula, as much of the binder and glass beads attached to the whisk (mixer) as possible are removed and then stirred into the glass beads/binder mixture in the mixing bowl. The sides of the bowl are then scraped to mix in any excess binder that might have accumulated on the sides. At this point, the glass beads/hexamethylenediamine-dextrose binder mixture is ready for molding in a shell bone mold.

The slides of the shell bone mold are confirmed to be aligned within the bottom mold platen. Using a large spatula, a glass beads/hexamethylenediamine-dextrose binder mixture is then quickly added into the three mold cavities within the shell bone mold. The surface of the mixture in each cavity is flattened out, while scraping off the excess mixture to give a uniform surface area to the shell bone. Any inconsistencies or gaps that existed in any of the cavities are filled in with additional glass beads/hexamethylenediamine-dextrose binder mixture and then flattened out. Once a glass beads/hexamethylenediamine-dextrose binder mixture is placed into the shell bone cavities, and the mixture is exposed to heat, curing begins. As manipulation time can affect test results, e.g., shell bones with two differentially cured layers can be produced; shell bones are prepared consistently and rapidly. With the shell bone mold filled, the top platen is quickly placed onto the bottom platen. At the same time, or quickly thereafter, measurement of curing time is initiated by means of a stopwatch, during which curing the temperature of the bottom platen ranged from about 400° F. to about 430° F., while the temperature of the top platen ranged from about 440° F. to about 470° F. At seven minutes elapsed time, the top platen is removed and the slides pulled out so that all three shell bones can be removed. The freshly made shell bones are then placed on a wire rack, adjacent to the shell bone mold platen, and allowed to cool to room temperature. Thereafter, each shell bone is labeled and placed individually in a plastic storage bag labeled appropriately. If shell bones can not be tested on the day they were prepared, the shell bone-containing plastic bags were placed in a desiccator unit.

Conditioning (Weathering) Procedure for Shell Bones: A Blue M humidity chamber is turned on and then set to provide weathering conditions of 90° F. and 90% relative humidity (i.e., 90° F./90% rH). The water tank on the side of the humidity chamber is checked and filled regularly, usually each time it is turned on. The humidity chamber is allowed to reach the specified weathering conditions over a period of at least 4 hours, with a day-long equilibration period being typical. Shell bones to be weathered are loaded quickly (since while the doors are open both the humidity and the temperature decrease), one at a time through the open humidity chamber doors, onto the upper, slotted shelf of the humidity chamber. The time that the shell bones are placed in the humidity chamber is noted, and weathering is conducted for a period of 24 hours. Thereafter, the humidity chamber doors are opened and one set of shell bones at a time are quickly removed and placed individually into respective plastic storage bags, being sealed completely. Generally, one to four sets of shell bones at a time are weathered as described above. Weathered shell bones are immediately taken to the Instron room and tested.

Test Procedure for Breaking Shell Bones: In the Instron room, the shell bone test method is loaded on the 5500 R Instron machine while ensuring that the proper load cell is installed (i.e., Static Load Cell 5 kN), and the machine is allowed to warm up for fifteen minutes. During this period of time, shell bone testing grips are verified as being installed on the machine. The load cell is zeroed and balanced, and then one set of shell bones is tested at a time as follows: A shell bone is removed from its plastic storage bag and then weighed. The weight (in grams) is then entered into the computer associated with the Instron machine. The measured thickness of the shell bone (in inches) is then entered, as specimen thickness, three times into the computer associated with the Instron machine. A shell bone specimen is then placed into the grips on the Instron machine, and testing initiated via the keypad on the Instron machine. After removing a shell bone specimen, the measured breaking point is entered into the computer associated with the Instron machine, and testing continued until all shell bones in a set are tested.

Carbohydrate Reactant: Polyamine Ratio Effect on Shell Bone Properties. Shell Bones were made with varying ratios of dextrose monohydrate (DMH) to Hexamethylenediamine (HMDA) with a silane additive (ISIO200) were examined as described above, at a test speed of 25 mm/min. The weight ratios tested include 90/10, 85/15, 80/20 and 75/25, respectively.

| | Stress at peak/MNm$^{-2}$ | | Strength Loss/% |
|---|---|---|---|
| | Dry | Weathered | |
| 90% DMH + 10% HMDA + 0.3% ISIO200, pH 11.06 | 2.954 | 1.929 | 34.69 |
| 85% DMH + 15% HMDA + 0.3% ISIO200, pH 11.29 | 2.573 | 2.017 | 21.61 |
| 80% DMH + 20% HMDA + 0.3% ISIO200, pH 11.54 | 2.747 | 2.344 | 14.68 |
| 75% DMH + 25% HMDA + 0.3% ISIO200, pH 11.71 | 2.735 | 2.073 | 24.21 |

Example: Glass Wool (Fiber Glass) Trials

Comparisons of the qualities of two glucose—hexamethylenediamine binders with a standard binder in terms of curing and rigidity on a glass wool product (Ac+032 100 mm 1200 mm width; 32 kg/m$^3$-15 m/min) were carried out by measuring the parting strength and density.

Binder 1: 85% glucose—15% hexamethylenediamine.
Binder 2: 90% glucose—10% hexamethylenediamine.

Ordinary Parting Strength (Before Autoclave) and Weathered Parting Strength (After Autoclave) may be measured as described in International Patent Application, Publication Number WO 2008/089851 or WO2009/019235:

Parting Strength on a Standard Binder:

| | BEFORE AUTOCLAVE | | | | AFTER AUTOCLAVE | | |
|---|---|---|---|---|---|---|---|
| | Weight (g) | Force (N) | density (kg/m$^3$) | | Weight (g) | Force (N) | density (kg/m$^3$) |
| 1 | 21.90 | 72.0 | 34.5 | 7 | 22.00 | 48.8 | 34.6 |
| 2 | 21.00 | 64.0 | 33.1 | 8 | 21.00 | 50.7 | 33.1 |

-continued

|   | BEFORE AUTOCLAVE | | | AFTER AUTOCLAVE | | | |
|---|---|---|---|---|---|---|---|
|   | Weight (g) | Force (N) | density (kg/m$^3$) |   | Weight (g) | Force (N) | density (kg/m$^3$) |
| 3 | 18.20 | 51.7 | 28.7 | 9 | 19.80 | 46.0 | 31.2 |
| 4 | 18.80 | 53.0 | 29.6 | 10 | 17.90 | 35.6 | 28.2 |
| 5 | 19.90 | 50.6 | 31.3 | 11 | 20.10 | 52.5 | 31.7 |
| 6 | 20.40 | 60.5 | 32.1 | 12 | 19.70 | 43.9 | 31.0 |
| Total | 120.20 | 351.8 | 31.6 | Total | 120.50 | 277.5 | 31.6 |
|   |   | 35861.4 g |   |   |   | 28287.5 g |   |

P.S. BEFORE: 298.3 gf/gwt
P.S. AFTER: 234.8 gf/gwt
LOSS: 63.6 gf/gwt ie 21.3%

Parting Strength on Binder 1:

|   | BEFORE AUTOCLAVE | | | AFTER AUTOCLAVE | | | |
|---|---|---|---|---|---|---|---|
|   | Weight (g) | Force (N) | density (kg/m$^3$) |   | Weight (g) | Force (N) | density (kg/m$^3$) |
| 1 | 22.00 | 95.6 | 34.6 | 7 | 19.80 | 50.0 | 31.2 |
| 2 | 18.70 | 53.9 | 29.5 | 8 | 17.80 | 46.7 | 28.0 |
| 3 | 18.20 | 63.9 | 28.7 | 9 | 17.80 | 51.2 | 28.0 |
| 4 | 18.10 | 62.6 | 28.5 | 10 | 20.50 | 59.3 | 32.3 |
| 5 | 20.50 | 75.0 | 32.3 | 11 | 18.40 | 46.0 | 29.0 |
| 6 | 18.70 | 60.3 | 29.5 | 12 | 18.60 | 47.3 | 29.3 |
| Total | 116.20 | 411.3 | 30.5 | Total | 112.90 | 300.5 | 29.6 |
|   |   | 41926.6 g |   |   |   | 30632.0 g |   |

P.S. BEFORE: 360.8 gf/gwt
P.S. AFTER: 271.3 gf/gwt
LOSS: 89.5 gf/gwt ie 24.8%

Parting Strength on Binder 2:

|   | BEFORE AUTOCLAVE | | | AFTER AUTOCLAVE | | | |
|---|---|---|---|---|---|---|---|
|   | Weight (g) | Force (N) | density (kg/m$^3$) |   | Weight (g) | Force (N) | density (kg/m$^3$) |
| 1 | 18.50 | 51.5 | 29.1 | 7 | 19.40 | 52.2 | 30.6 |
| 2 | 19.50 | 64.5 | 30.7 | 8 | 20.10 | 52.7 | 31.7 |
| 3 | 21.30 | 75.6 | 33.5 | 9 | 19.30 | 54.5 | 30.4 |
| 4 | 20.80 | 78.8 | 32.8 | 10 | 19.80 | 57.2 | 31.2 |
| 5 | 19.80 | 64.4 | 31.2 | 11 | 19.80 | 58.2 | 31.2 |
| 6 | 18.40 | 70.0 | 29.0 | 12 | 18.80 | 51.9 | 29.6 |
| Total | 118.30 | 404.8 | 31.1 | Total | 117.20 | 326.7 | 30.8 |
|   |   | 41264.0 g |   |   |   | 33302.8 g |   |

P.S. BEFORE: 348.8 gf/gwt
P.S. AFTER: 284.2 gf/gwt
LOSS: 78.1 gf/gwt ie 19.3%

Observations during the trial: The product was browner on the line with the two glucose–hexamethylenediamine binders.

Conclusions: With the two glucose—hexamethylenediamine binders, the parting strength (which is a longitudinal tensile strength) results showed a significant improvement; and a significant improvement was observed in three other rigidity tests ("60°" test—sagging measured when leaned at 60° against a chute; "table" test—sagging measured against a horizontal plane; and Acermi test—sagging measured 35 cm from the edge of a table).

Example: Particle Board Trial

Comparisons of the qualities of particle boards made using a urea-formaldehyde binder (UF E0) and using a carbohydrate polyamine (hexamethylenediamine) binder were carried out under the following conditions.

Board size: 350×333 mm and mainly 10 mm thick (2×20 mm).

Platen temperature: 195° C. mainly but also, 175 and ~215° C.

Pressure: 3.5 Mpa (35 bar) Quoted—Actual 35 Kg/cm$^2$, 56 bar to achieve.

Density target: 650 kg/m³
Pre-form prepared prior to pressing.
Results:

| Binder | PressTime (secs) | IB Strength (Mpa) |
|---|---|---|
| UF E0 | 150 | 0.75 |
|  | 100 | 0.69 |
|  | 80 | 0.66 |
| Carbohydrate polyamine | 300 | 0.92 |
|  | 240 | 0.99 |
|  | 180 | 0.88 |
|  | 150 | 0.73 |
|  | 120 | 0.68 |
|  | 90 | 0.15 |

All boards prepared appeared of high quality; no splits or degassing were observed. The boards made with this carbohydrate polyamine formulation match urea formaldehyde board when they are cured for 150 seconds.

The invention claimed is:

1. A method of making a collection of matter bound with a cured, thermoset, polymeric binder, the method comprising:
   (i) preparing an aqueous binder solution containing reactants for producing the cured, thermoset, polymeric binder, wherein the reactants include a reducing sugar and a nucleophile $R_1$-Q-$R_2$ wherein
   Q is alkyl, cycloalkyl, heteroalkyl, or cycloheteroalkyl, each of which is optionally substituted,
   $R_1$ is an amine and
   $R_2$ is selected from the group consisting of an imine, a nitro, a phosphate, a phosphono, a hydroxyl, a sulpho, a sulfinyl, a cyanate, an isocyanate, a thiol, a halogen, a haloformyl, a carboxyl, a carboxylate, and an alkoxide;
   (ii) disposing the solution onto said collection of matter; and
   (iii) drying the binder solution to form an uncured binder and thermally curing the uncured binder to form the collection of matter bound with the cured, thermoset, polymeric binder.

2. The method of claim 1, wherein the collection of matter comprises matter selected from the group consisting of glass fibers, mineral fibers, aramid fibers, ceramic fibers, metal fibers, carbon fibers, polyimide fibers, polyester fibers, rayon fibers, cellulosic fibers, wood shavings, sawdust, wood pulp, ground wood, jute, flax, hemp, straw, particulates, coal particulates and sand particulates.

3. The method of claim 1, wherein the collection of matter comprises glass fibers.

4. The method of claim 3, wherein the glass fibers are present in the range from about 70% to about 99% by weight.

5. The method of claim 1, wherein the collection of matter bound with the cured, thermoset, polymeric binder is a composite wood board.

6. The method of claim 1, wherein the weight ratio of the reducing sugar to the nucleophile is in the range of about 2:1 to about 10:1.

7. The method of claim 1, wherein preparing the aqueous binder solution includes adjusting the pH of the binder solution to within the range of about 8 to about 12.

8. The method of claim 1, wherein the method has at least one of the following features:
   the reducing sugar is a polysaccharide;
   the reducing sugar is a monosaccharide or a disaccharide;
   the reducing sugar is a monosaccharide in its aldose or ketose form;
   the reducing sugar is selected from the group consisting of dextrose, xylose, fructose, dihydroxyacetone, and mixtures thereof.

9. The method of claim 1, wherein the method has at least one of the following features:
   Q is an alkyl selected from the group consisting of $C_2$-$C_{24}$;
   Q is an alkyl selected from the group consisting of $C_2$-$C_8$;
   Q is an alkyl selected from the group consisting of $C_3$-$C_7$;
   Q is a $C_6$ alkyl;
   Q is alkyl, cycloalkyl, heteroalkyl, or cycloheteroalkyl, each of which is not substituted
   Q is alkyl, cycloalkyl, heteroalkyl, or cycloheteroalkyl, each of which is optionally substituted by a group selected from the group consisting of hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof;
   Q is selected from the group consisting of a cyclohexyl, cyclopentyl and cyclobutyl;
   $R_1$-Q-$R_2$ is 2-[(2-aminoethyl)amino]ethanol.

10. The method of claim 1, wherein a mole ratio of the reducing sugar to the nucleophile is in the range of about 1:1 to about 30:1.

11. The method of claim 1, wherein a mole ratio of the reducing sugar to the nucleophile is in the range of about 2:1 to about 10:1.

12. The method of claim 1, wherein $R_1$ and $R_2$ form covalent bonds with the reducing sugar to form the polymeric binder.

13. The method of claim 1, wherein the cured, thermoset, polymeric binder is formaldehyde-free.

14. The method of claim 1, wherein neither formaldehyde nor phenol is used as a reagent.

15. The method of claim 1, wherein $R_2$ is selected from the group consisting of an imine, a phosphate, a phosphono, a hydroxyl, a sulpho, a sulfinyl, a cyanate, a thiol, a carboxyl, and a carboxylate.

16. The method of claim 1, wherein the mole ratio of the reducing sugar to the nucleophile is in the range of 3:1 to 6:1.

17. The method of claim 1, wherein the aqueous binder solution has an alkaline pH.

18. The method of claim 1, wherein the cured, thermoset, polymeric binder is substantially water insoluble.

19. The method of claim 1, wherein the cured, thermoset, polymeric binder is essentially acid-free.

* * * * *